(12) United States Patent
Pevzner et al.

(10) Patent No.: US 10,835,488 B2
(45) Date of Patent: Nov. 17, 2020

(54) STABLE ORALLY DISINTEGRATING PHARMACEUTICAL COMPOSITIONS

(71) Applicant: DEXCEL PHARMA TECHNOLOGIES LTD., Or-Akiva (IL)

(72) Inventors: Victor Pevzner, Hadera (IL); Sheera Moses-Heller, Atlit (IL)

(73) Assignee: DEXCEL PHARMA TECHNOLOGIES LTD., Or-Akiva (IL)

( * ) Notice: Subject to any disclaimer, the term of this patent is extended or adjusted under 35 U.S.C. 154(b) by 0 days.

(21) Appl. No.: 16/130,494

(22) Filed: Sep. 13, 2018

(65) Prior Publication Data

US 2019/0008767 A1 Jan. 10, 2019

Related U.S. Application Data

(63) Continuation of application No. 15/372,917, filed on Dec. 8, 2016, now Pat. No. 10,076,494.

(Continued)

(51) Int. Cl.
*A61K 9/00* (2006.01)
*A61P 1/04* (2006.01)
(Continued)

(52) U.S. Cl.
CPC .......... *A61K 9/0056* (2013.01); *A61K 9/2009* (2013.01); *A61K 9/2013* (2013.01);
(Continued)

(58) Field of Classification Search
CPC ............ A61K 2300/00; A61K 31/4439; A61K 31/44; A61K 9/5078; A61K 9/2081; A61K 9/5026; A61K 47/02; A61K 9/1611; A61K 9/2009; A61K 9/0056; A61K 9/2886; A61K 45/06; A61K 31/415; A61K 33/00; A61K 36/185; A61K 36/534; A61K 9/1652; A61K 9/2054; A61K 9/5073; A61K 9/4808; A61K 9/1635; A61K 9/209; A61K 9/2866; A61K 31/195; A61K 9/1617; A61K 9/2013; A61K 9/2846; A61K 9/5084; A61K 31/70; A61K 9/0007; A61K 9/2077; A61K 36/42; A61K 36/48; A61K 36/74; A61K 36/82; A61K 36/898; A61K 9/0019; A61K 9/0095; A61K 9/1623; A61K 9/2086; A61K 9/5047; A61K 31/445; A61K 9/1694; A61K 9/2018; A61K 9/4858; A61K 9/4891; A61K 31/00; A61K 31/4184; A61K 9/2095; A61K 9/2813; A61K 31/165; A61K 31/34; A61K 31/569; A61K 31/7048; A61K 47/40; A61K 9/0065; A61K 9/1075; A61K 9/1688; A61K 9/284; A61K 9/4866; A61K 9/5042; A61K 31/138; A61K 31/19; A61K 31/192; A61K 31/426; A61K 31/485; A61K 31/60; A61K 47/10; A61K 47/18; A61K 47/183; A61K 47/22; A61K 47/6951; A61K 9/06; A61K 9/145; A61K 9/146; A61K 9/2027; A61K 9/2059; A61K 9/28; A61K 9/4816; A61K 9/485; A61K 9/5015; A61K 9/5031; A61K 9/5036; A61K 9/70; A61K 2035/122; A61K 2035/128; A61K 2800/5422; A61K 31/137; A61K 31/18; A61K 31/196; A61K 31/20; A61K 31/216; A61K 31/341; A61K 31/351; A61K 31/355; A61K 31/366; A61K 31/381; A61K 31/41; A61K 31/4164; A61K 31/4178; A61K 31/444; A61K 31/4458; A61K 31/4545; A61K 31/519; A61K 31/522; A61K 31/542; A61K 31/5513; A61K 31/5517; A61K 31/56; A61K 31/57; A61K 31/58; A61K 31/606; A61K 31/616; A61K 31/635; A61K 31/7135; A61K 38/13; A61K 47/20; A61K 47/26; A61K 47/32; A61K 47/36; A61K 47/38; A61K 47/42;

(Continued)

(56) References Cited

U.S. PATENT DOCUMENTS 2,757,124 A 7/1956 Wolff
3,119,742 A 1/1964 Heimlich
(Continued)

FOREIGN PATENT DOCUMENTS

CN 1961868 A 5/2007
DE 19752843 A1 7/1999
(Continued)

OTHER PUBLICATIONS

Jeganathan ("Interpolyelectrolyte Complexes of EudragitTM EPO with Hypromellose Acetate Succinate and EudragitTM EPO with Hypromellose Phthalate as Potential Carriers for Oral Controlled Drug Delivery", AAPS PharmSciTech, vol. 16, No. 4, August (Year: 2015).*

(Continued)

*Primary Examiner* — Audrea B Coniglio
(74) *Attorney, Agent, or Firm* — Rothwell, Figg, Ernst & Manbeck, P.C.

(57) ABSTRACT

Described herein are stable orally disintegrating tablets containing a proton pump inhibitor, methods for making the same, and methods for treating subjects in need thereof. In particular, the orally disintegrating tablets are composed of a plurality of coated units admixed with a disintegrant that demonstrate decreased friability and increased hardness.

26 Claims, No Drawings

Related U.S. Application Data

(60) Provisional application No. 62/350,916, filed on Jun. 16, 2016.

(51) Int. Cl.
*A61K 9/20* (2006.01)
*A61K 31/4439* (2006.01)
*A61K 9/50* (2006.01)

(52) U.S. Cl.
CPC .......... *A61K 9/2018* (2013.01); *A61K 9/2027* (2013.01); *A61K 9/2054* (2013.01); *A61K 9/2081* (2013.01); *A61K 9/2095* (2013.01); *A61K 31/4439* (2013.01); *A61P 1/04* (2018.01); *A61K 9/5026* (2013.01); *A61K 9/5073* (2013.01)

(58) Field of Classification Search
CPC ...... A61K 8/0212; A61K 8/042; A61K 8/046; A61K 8/345; A61K 8/731; A61K 8/733; A61K 8/735; A61K 8/736; A61K 9/0004; A61K 9/0024; A61K 9/0031; A61K 9/0043; A61K 9/0053; A61K 9/006; A61K 9/0073; A61K 9/025; A61K 9/08; A61K 9/127; A61K 9/14; A61K 9/1641; A61K 9/19; A61K 9/2031; A61K 9/205; A61K 9/2072; A61K 9/282; A61K 9/286; A61K 9/2893; A61K 9/50; A61K 9/5161; A61K 9/5192; A61P 1/04; A61P 1/00; A61P 43/00; A61P 29/00; A61P 31/04; A61P 15/00; A61P 25/00; A61P 11/00; A61P 19/02; A61P 1/14; A61P 25/04; A61P 25/24; A61P 25/26; A61P 35/00; A61P 9/12; A61P 11/04; A61P 15/02; A61P 15/06; A61P 1/06; A61P 31/00; A61P 31/10; A61P 31/12; A61P 37/02; A61P 37/06; A61P 3/10; A61P 5/24; A61P 7/10; A61P 9/10; A61P 5/26; A61L 15/28; A61L 27/20; A61L 26/0023; A61L 27/26; A61L 27/52; A61L 15/32; A61L 15/425; A61L 15/44; A61L 15/60; A61L 17/005; A61L 2300/114; A61L 2300/204; A61L 2300/214; A61L 2300/236; A61L 2300/406; A61L 2300/41; A61L 2300/43; A61L 2300/434; A61L 2300/45; A61L 2300/604; A61L 2300/62; A61L 2430/40; A61L 26/0071; A61L 26/008; A61L 26/0085; A61L 27/222; A61L 27/3683; A61L 27/38; A61L 27/502; A61L 27/54; A61L 27/56; A61L 29/085

See application file for complete search history.

(56) References Cited

U.S. PATENT DOCUMENTS

| | | |
|---|---|---|
| 4,045,563 A | 8/1977 | Berntsson |
| 4,255,431 A | 3/1981 | Junggren |
| 4,359,465 A | 11/1982 | Ruwart |
| 4,472,409 A | 9/1984 | Senn-Bilfinger |
| 4,508,905 A | 4/1985 | Junggren |
| 4,547,359 A | 10/1985 | Zierenberg |
| 4,628,098 A | 12/1986 | Nohara |
| 4,666,703 A | 5/1987 | Kopf |
| 4,689,333 A | 8/1987 | Nohara |
| 4,710,384 A | 12/1987 | Rotman |
| 4,738,974 A | 4/1988 | Brandstrom |
| 4,738,975 A | 4/1988 | Nohara |
| 4,749,575 A | 6/1988 | Rotman |
| 4,786,505 A | 11/1988 | Lovgren |
| 4,840,799 A | 6/1989 | Appelgren |
| 4,853,230 A | 8/1989 | Lovgren |
| 4,871,549 A | 10/1989 | Ueda |
| 4,874,614 A | 10/1989 | Becker |
| 4,888,178 A | 12/1989 | Rotini |
| 4,940,588 A | 7/1990 | Sparks |
| 4,950,484 A | 8/1990 | Olthoff |
| 5,006,344 A | 4/1991 | Jerzewski |
| 5,013,557 A | 5/1991 | Tai |
| 5,013,743 A | 5/1991 | Iwahi |
| 5,026,560 A | 6/1991 | Makino |
| 5,045,321 A | 9/1991 | Makino |
| 5,045,552 A | 9/1991 | Souda |
| 5,055,306 A | 10/1991 | Barry |
| 5,073,374 A | 12/1991 | McCarty |
| 5,093,132 A | 3/1992 | Makino |
| 5,215,756 A | 6/1993 | Gole |
| 5,219,870 A | 6/1993 | Kim |
| 5,225,202 A | 7/1993 | Hodges |
| 5,232,706 A | 8/1993 | Palomo |
| 5,244,670 A | 9/1993 | Upson |
| 5,288,506 A | 2/1994 | Spickett |
| 5,312,824 A | 5/1994 | Sohda |
| 5,328,697 A | 7/1994 | Raman |
| 5,362,424 A | 11/1994 | Lee |
| 5,385,739 A | 1/1995 | Debregeas et al. |
| 5,399,700 A | 3/1995 | Min |
| 5,409,711 A | 4/1995 | Mapelli |
| 5,433,959 A | 7/1995 | Makino |
| 5,464,632 A | 11/1995 | Cousin |
| 5,508,041 A | 4/1996 | Lee |
| 5,508,276 A | 4/1996 | Anderson |
| 5,518,730 A | 5/1996 | Fuisz |
| 5,536,735 A | 7/1996 | Takechi |
| 5,554,147 A | 9/1996 | Batich |
| 5,582,837 A | 12/1996 | Shell |
| 5,599,794 A | 2/1997 | Eek |
| 5,622,717 A | 4/1997 | Fuisz |
| 5,626,875 A | 5/1997 | Ballester Rodes |
| 5,639,478 A | 6/1997 | Makino |
| 5,690,960 A | 11/1997 | Bengtsson |
| 5,708,017 A | 1/1998 | Dave |
| 5,725,886 A | 3/1998 | Erkoboni |
| 5,731,002 A | 3/1998 | Olovson |
| 5,753,265 A | 5/1998 | Bergstrand |
| 5,780,057 A | 7/1998 | Conte |
| 5,783,215 A | 7/1998 | Arwidsson |
| 5,788,678 A | 8/1998 | Van Antwerp |
| 5,798,120 A | 8/1998 | Tomohisa |
| 5,807,583 A | 9/1998 | Kristensen |
| 5,814,338 A | 9/1998 | Veronesi |
| 5,817,338 A | 10/1998 | Bergstrand |
| 5,824,339 A | 10/1998 | Shimizu |
| 5,840,737 A | 11/1998 | Phillips |
| 5,855,914 A | 1/1999 | Koyama |
| 5,869,098 A | 2/1999 | Misra |
| 5,879,708 A | 3/1999 | Makino |
| 5,900,424 A | 5/1999 | Kallstrom |
| 5,945,124 A | 8/1999 | Sachs |
| 5,968,551 A | 10/1999 | Oshlack |
| 5,972,389 A | 10/1999 | Shell |
| 5,985,322 A | 11/1999 | Anderson |
| 5,997,903 A | 12/1999 | Dietrich |
| 6,013,281 A | 1/2000 | Lundberg |
| 6,017,560 A | 1/2000 | Makino |
| 6,022,562 A | 2/2000 | Autant |
| 6,024,222 A | 2/2000 | Friberg |
| 6,068,856 A | 5/2000 | Sachs |
| 6,077,541 A | 6/2000 | Chen |
| 6,090,827 A | 7/2000 | Erickson |
| 6,092,660 A | 7/2000 | Rune |
| 6,096,340 A | 8/2000 | Chen |
| 6,113,941 A | 9/2000 | Takada |
| 6,123,962 A | 9/2000 | Makino |
| 6,132,770 A | 10/2000 | Lundberg |
| 6,132,771 A | 10/2000 | Depui |
| 6,136,344 A | 10/2000 | Depui |
| 6,149,942 A | 11/2000 | Scheiwe |
| 6,150,380 A | 11/2000 | Lovqvist |

(56) References Cited

U.S. PATENT DOCUMENTS

| | | | |
|---|---|---|---|
| 6,159,499 A | 12/2000 | Seth | |
| 6,165,512 A | 12/2000 | Mezaache | |
| 6,174,548 B1 | 1/2001 | Chen | |
| 6,183,776 B1 | 2/2001 | Depui et al. | |
| 6,191,148 B1 | 2/2001 | McManus | |
| 6,207,198 B1 | 3/2001 | Seth | |
| 6,228,400 B1 | 5/2001 | Lee | |
| 6,231,888 B1 | 5/2001 | Lerner | |
| 6,245,351 B1 | 6/2001 | Nara | |
| 6,248,355 B1 | 6/2001 | Seth | |
| 6,248,758 B1 | 6/2001 | Klokkers | |
| 6,262,085 B1 | 7/2001 | Whittle | |
| 6,268,385 B1 | 7/2001 | Whittle | |
| 6,270,804 B1 | 8/2001 | Getz | |
| 6,274,173 B1 | 8/2001 | Sachs | |
| 6,284,271 B1 | 9/2001 | Lundberg | |
| 6,294,192 B1 | 9/2001 | Patel | |
| 6,296,875 B1 | 10/2001 | Makino | |
| 6,296,876 B1 | 10/2001 | Odidi | |
| 6,316,029 B1 | 11/2001 | Jain | |
| 6,316,481 B1 | 11/2001 | Freehauf | |
| 6,326,384 B1 | 12/2001 | Whittle | |
| 6,328,993 B1 | 12/2001 | Linder | |
| 6,328,994 B1 | 12/2001 | Shimizu | |
| 6,344,215 B1 | 2/2002 | Bettman | |
| 6,346,269 B1 | 2/2002 | Hsiao | |
| 6,365,184 B1 | 4/2002 | Depui | |
| 6,372,254 B1 | 4/2002 | Ting | |
| 6,379,705 B1 | 4/2002 | Mendes | |
| 6,380,234 B1 | 4/2002 | Makino | |
| 6,383,471 B1 | 5/2002 | Chen | |
| 6,391,342 B1 | 5/2002 | Henriksen | |
| 6,395,300 B1 | 5/2002 | Straub | |
| 6,403,616 B1 | 6/2002 | Erickson | |
| 6,426,369 B1 | 7/2002 | Sato | |
| 6,428,809 B1 | 8/2002 | Abrams | |
| 6,428,810 B1 | 8/2002 | Bergstrand | |
| 6,479,075 B1 | 11/2002 | Odidi | |
| 6,489,346 B1 | 12/2002 | Phillips | |
| 6,489,646 B1 | 12/2002 | Phillips | |
| 6,500,459 B1 | 12/2002 | Chhabra | |
| 6,521,256 B2 | 2/2003 | Makino | |
| 6,544,556 B1 | 4/2003 | Chen | |
| 6,551,621 B1 | 4/2003 | Debregeas | |
| 6,558,704 B1 | 5/2003 | Bartholomaeus | |
| 6,569,453 B2 | 5/2003 | Linder | |
| 6,576,258 B1 | 6/2003 | Kofler | |
| 6,586,004 B2 | 7/2003 | Shimizu | |
| 6,589,556 B2 | 7/2003 | Cherukuri | |
| 6,596,315 B1 | 7/2003 | Boissier | |
| 6,599,529 B1 | 7/2003 | Skinhoej | |
| 6,602,522 B1 | 8/2003 | Chen | |
| 6,605,303 B1 | 8/2003 | Karehill | |
| 6,610,323 B1 | 8/2003 | Lundberg | |
| 6,613,354 B2 | 9/2003 | Depui | |
| 6,623,759 B2 | 9/2003 | Heese | |
| 6,627,219 B2 | 9/2003 | Hao | |
| 6,627,223 B2 | 9/2003 | Percel | |
| 6,638,534 B1 | 10/2003 | Ishibashi | |
| 6,645,528 B1 | 11/2003 | Straub | |
| 6,645,988 B2 | 11/2003 | Phillips | |
| 6,699,885 B2 | 3/2004 | Phillips | |
| 6,706,285 B1 | 3/2004 | Woo | |
| 6,713,079 B2 | 3/2004 | Usala | |
| 6,720,001 B2 | 4/2004 | Chen | |
| 6,726,927 B2 | 4/2004 | Chen | |
| 6,730,685 B1 | 5/2004 | Bruells | |
| 6,733,778 B1 | 5/2004 | Chen | |
| 6,740,339 B1 | 5/2004 | Ohkouchi | |
| 6,749,864 B2 | 6/2004 | Makino | |
| 6,749,867 B2 | 6/2004 | Robinson | |
| 6,780,435 B2* | 8/2004 | Chen | A61K 9/5078 424/400 |
| 6,780,436 B1 | 8/2004 | Lopez-Cabrera | |
| 6,780,881 B2 | 8/2004 | Linder | |
| 6,780,882 B2 | 8/2004 | Phillips | |
| 6,855,336 B2 | 2/2005 | Chen | |
| 6,869,615 B2 | 3/2005 | Chen | |
| 6,884,437 B2 | 4/2005 | Linder | |
| 6,897,205 B2 | 5/2005 | Beckert | |
| 6,923,988 B2 | 8/2005 | Patel | |
| 6,932,983 B1 | 8/2005 | Straub | |
| 6,960,357 B2* | 11/2005 | Chopra | A61K 9/2086 424/468 |
| 6,962,717 B1 | 11/2005 | Huber | |
| 6,982,281 B1 | 1/2006 | Chen | |
| 6,988,619 B1 | 1/2006 | Klatt | |
| 7,041,316 B2 | 5/2006 | Chen | |
| 7,070,805 B2 | 7/2006 | Shimizu | |
| 7,105,180 B2 | 9/2006 | Schmitt | |
| 7,118,765 B2 | 10/2006 | Norman | |
| 7,147,869 B2 | 12/2006 | Dietrich | |
| 7,217,429 B2 | 5/2007 | Garcia | |
| 7,223,421 B2 | 5/2007 | McTeigue | |
| 7,255,878 B1 | 8/2007 | Lahav | |
| 7,276,253 B2 | 10/2007 | Heese | |
| 7,351,723 B2 | 4/2008 | Linder | |
| 7,357,943 B2 | 4/2008 | Linder | |
| 7,399,485 B1 | 7/2008 | Shimizu | |
| 7,419,996 B2 | 9/2008 | Chow | |
| 7,431,942 B2 | 10/2008 | Shimizu | |
| 7,476,403 B2 | 1/2009 | Li | |
| 7,641,050 B2 | 1/2010 | Klatt | |
| 7,674,837 B2 | 3/2010 | Gaserod | |
| 7,732,474 B2 | 6/2010 | Muskulus | |
| 7,749,533 B2 | 7/2010 | Fu | |
| 7,815,940 B2 | 10/2010 | Pettersson | |
| 7,838,033 B2 | 11/2010 | Tanaka | |
| 7,875,292 B2 | 1/2011 | Shimizu | |
| 7,932,258 B2 | 4/2011 | Petereit | |
| 7,943,167 B2 | 5/2011 | Kulkarni | |
| 7,951,398 B2 | 5/2011 | Dietrich | |
| 7,988,999 B2 | 8/2011 | Dietrich | |
| 8,075,872 B2 | 12/2011 | Arkenau-Maric | |
| 8,093,271 B2 | 1/2012 | Los | |
| 8,101,209 B2 | 1/2012 | Legrand | |
| 8,105,626 B2 | 1/2012 | Shimizu | |
| 8,173,158 B2 | 5/2012 | Lee | |
| 8,187,617 B2 | 5/2012 | Howard | |
| 8,303,868 B2 | 11/2012 | Maruyama | |
| 8,309,136 B2 | 11/2012 | Cooper | |
| 8,329,744 B2 | 12/2012 | Badul | |
| 8,343,978 B2 | 1/2013 | Dong | |
| 8,383,154 B2 | 2/2013 | Bar-Shalom | |
| 8,409,612 B1 | 4/2013 | Criere | |
| 8,449,911 B2 | 5/2013 | Yoneyama | |
| 8,486,450 B2 | 7/2013 | Higuchi | |
| 8,530,463 B2 | 9/2013 | Cartt | |
| 8,530,500 B2 | 9/2013 | Juvonen | |
| 8,541,024 B2 | 9/2013 | Ono | |
| 8,545,881 B2 | 10/2013 | Venkatesh | |
| 8,461,187 B2 | 11/2013 | Taneja | |
| 8,685,448 B2 | 4/2014 | Santanach-Delisau | |
| 8,697,097 B2 | 4/2014 | Nonomura | |
| 8,715,730 B2 | 5/2014 | Takaki | |
| 8,765,176 B2 | 7/2014 | Yamamoto | |
| 8,771,729 B2 | 7/2014 | Perrett | |
| 8,846,698 B2 | 9/2014 | Andrews | |
| 8,865,212 B2 | 10/2014 | Ghosh | |
| 8,871,273 B2 | 10/2014 | Nagahara | |
| 8,877,746 B2 | 11/2014 | Chen | |
| 8,883,206 B2 | 11/2014 | Dokou | |
| 8,911,787 B2 | 12/2014 | Gandhi | |
| 8,968,776 B2 | 3/2015 | Seth | |
| 8,980,322 B2 | 3/2015 | Nagahara | |
| 8,993,599 B2 | 3/2015 | Hall | |
| 8,999,384 B2 | 4/2015 | Shafee | |
| 9,060,930 B2 | 6/2015 | Prinderre | |
| 9,060,936 B2 | 6/2015 | Berndl | |
| 9,198,862 B2 | 12/2015 | Pilgaonkar | |
| 9,237,760 B2 | 1/2016 | Ravishankar | |
| 9,241,910 B2 | 1/2016 | Kurasawa | |
| 9,254,268 B2 | 2/2016 | Temtsin Krayz | |
| 9,283,192 B2 | 3/2016 | Mullen | |

(56) References Cited

U.S. PATENT DOCUMENTS

| | | |
|---|---|---|
| 9,364,429 B2 | 6/2016 | Tsue |
| 9,486,446 B2 | 11/2016 | Kurasawa |
| 9,526,789 B2 | 12/2016 | Park |
| 2001/0024658 A1 | 9/2001 | Chen |
| 2001/0053387 A1 | 12/2001 | Hamied |
| 2002/0004071 A1 | 1/2002 | Cherukuri |
| 2002/0039597 A1 | 4/2002 | Ukai |
| 2002/0039598 A1 | 4/2002 | Makino |
| 2002/0045646 A1 | 4/2002 | Phillips |
| 2002/0054913 A1 | 5/2002 | Heese |
| 2002/0086029 A1 | 7/2002 | Lundberg |
| 2002/0098242 A1 | 7/2002 | Dardar |
| 2002/0128293 A1 | 9/2002 | Rampal |
| 2002/0137771 A1 | 9/2002 | Makino |
| 2002/0142034 A1 | 10/2002 | Shimizu |
| 2002/0147208 A1 | 10/2002 | Fleshner-Barak |
| 2002/0155067 A1 | 10/2002 | MacGregor |
| 2002/0160046 A1 | 10/2002 | Robinson |
| 2003/0091643 A1 | 5/2003 | Friesen |
| 2003/0096791 A1 | 5/2003 | Gupte |
| 2003/0113376 A1 | 6/2003 | Chen |
| 2003/0175348 A1 | 9/2003 | Kofler |
| 2003/0211155 A1 | 11/2003 | Makino |
| 2003/0219479 A1 | 11/2003 | Chen |
| 2003/0228363 A1 | 12/2003 | Patel |
| 2003/0236285 A1 | 12/2003 | Patel |
| 2004/0018235 A1 | 1/2004 | Tanizawa |
| 2004/0028737 A1 | 2/2004 | Deshpande |
| 2004/0029777 A1 | 2/2004 | Ando |
| 2004/0109894 A1 | 6/2004 | Shefer |
| 2004/0126422 A1 | 7/2004 | Tony Yu |
| 2004/0131675 A1 | 7/2004 | Yamamoto |
| 2004/0166162 A1 | 8/2004 | Niecestro |
| 2004/0175427 A1 | 9/2004 | Chen |
| 2004/0185111 A1 | 9/2004 | Rubino |
| 2004/0202714 A1 | 10/2004 | Nomura |
| 2004/0209919 A1 | 10/2004 | Makino |
| 2004/0213847 A1 | 10/2004 | Matharu |
| 2004/0219211 A1 | 11/2004 | Criere |
| 2004/0248942 A1 | 12/2004 | Hepburn |
| 2005/0043300 A1 | 2/2005 | Middleton |
| 2005/0053655 A1 | 3/2005 | Yang |
| 2005/0095285 A1 | 5/2005 | Rao |
| 2005/0095293 A1 | 5/2005 | Brauns |
| 2005/0106237 A1 | 5/2005 | Wuthrich |
| 2005/0112193 A1 | 5/2005 | Phillips |
| 2005/0136112 A1 | 6/2005 | Gonzales |
| 2005/0147668 A1 | 7/2005 | Bertelsen |
| 2005/0163846 A1 | 7/2005 | Aoki |
| 2005/0191353 A1 | 9/2005 | Krishna Antarkar |
| 2005/0214371 A1 | 9/2005 | Di Capua |
| 2005/0214372 A1 | 9/2005 | Di Capua |
| 2005/0232988 A1 | 10/2005 | Venkatesh |
| 2005/0232992 A1 | 10/2005 | Devane |
| 2005/0287211 A1 | 12/2005 | Yoshida |
| 2006/0018964 A1 | 1/2006 | Combessis |
| 2006/0051421 A1 | 3/2006 | Shterman |
| 2006/0078614 A1 | 4/2006 | Venkatesh |
| 2006/0105039 A1 | 5/2006 | Lai |
| 2006/0115530 A1 | 6/2006 | Pettersson |
| 2006/0134054 A1 | 6/2006 | Kulkarni |
| 2006/0134210 A1 | 6/2006 | Perrson |
| 2006/0153908 A1 | 7/2006 | Strong |
| 2006/0153918 A1 | 7/2006 | Lerner |
| 2006/0159756 A1 | 7/2006 | Sjoblom |
| 2006/0159762 A1 | 7/2006 | Stanic Ljubin |
| 2006/0177509 A1 | 8/2006 | Nagahara |
| 2006/0204568 A1 | 9/2006 | Dietrich |
| 2006/0216346 A1 | 9/2006 | Dietrich |
| 2006/0222701 A1 | 10/2006 | Kulkarni |
| 2006/0240100 A1 | 10/2006 | Anstett |
| 2006/0240103 A1 | 10/2006 | McCallister |
| 2006/0257467 A1 | 11/2006 | Kostadinov |
| 2006/0276500 A1 | 12/2006 | Phillips |
| 2007/0053981 A1 | 3/2007 | Blychert |
| 2007/0065513 A1 | 3/2007 | Ayramoff |
| 2007/0141151 A1 | 6/2007 | Silver |
| 2007/0148153 A1 | 6/2007 | Shlieout |
| 2007/0196486 A1 | 8/2007 | Vanderbist |
| 2007/0202169 A1 | 8/2007 | Silver |
| 2007/0231388 A1 | 10/2007 | Anstett-Klein |
| 2007/0259040 A1 | 11/2007 | Cherukuri |
| 2008/0003281 A1 | 1/2008 | Clemmensen |
| 2008/0014228 A1 | 1/2008 | Darmuzey |
| 2008/0014257 A1 | 1/2008 | He |
| 2008/0026051 A1 | 1/2008 | Lizio |
| 2008/0033027 A1 | 2/2008 | Bascomb |
| 2008/0050428 A1 | 2/2008 | Ney |
| 2008/0063710 A1 | 3/2008 | Suzuki |
| 2008/0069878 A1 | 3/2008 | Venkatesh |
| 2008/0095853 A1 | 4/2008 | Clemmensen |
| 2008/0102133 A1 | 5/2008 | Brueck-Scheffler |
| 2008/0145421 A1 | 6/2008 | Ukai |
| 2008/0175917 A1 | 7/2008 | Glad |
| 2008/0193522 A1 | 8/2008 | Meier |
| 2008/0214619 A1 | 9/2008 | Wolfe |
| 2008/0226684 A1 | 9/2008 | Peppas |
| 2008/0254112 A1 | 10/2008 | Klokkers |
| 2008/0254115 A1 | 10/2008 | Rubino |
| 2008/0305160 A1 | 12/2008 | Guimberteau |
| 2008/0305166 A1 | 12/2008 | Durig |
| 2008/0312168 A1 | 12/2008 | Pilgaonkar |
| 2009/0068261 A1 | 3/2009 | Reher |
| 2009/0068263 A1 | 3/2009 | Antarkar |
| 2009/0092658 A1 | 4/2009 | Hall |
| 2009/0148524 A1 | 6/2009 | Higuchi |
| 2009/0208576 A1 | 8/2009 | Gandhi |
| 2009/0220611 A1 | 9/2009 | Dargelas |
| 2009/0220613 A1 | 9/2009 | Odidi |
| 2009/0252787 A1 | 10/2009 | Pasha |
| 2009/0274756 A1 | 11/2009 | Ukai |
| 2009/0291136 A1 | 11/2009 | Stanic Ljubin |
| 2009/0304787 A1 | 12/2009 | Odidi |
| 2009/0317473 A1* | 12/2009 | Naringrekar ......... A61K 9/2009 424/487 |
| 2010/0015239 A1 | 1/2010 | Ahmed |
| 2010/0016382 A1 | 1/2010 | Nomura |
| 2010/0068268 A1 | 3/2010 | Rahmouni |
| 2010/0068291 A1 | 3/2010 | Caisse |
| 2010/0080849 A1 | 4/2010 | Schlutermann |
| 2010/0130542 A1 | 5/2010 | Phillips |
| 2010/0172969 A1 | 7/2010 | Dreu |
| 2010/0183710 A1 | 7/2010 | Bolugoddu |
| 2010/0221324 A1 | 9/2010 | Petereit |
| 2010/0247641 A1 | 9/2010 | Ranzani |
| 2010/0255091 A1 | 10/2010 | Ranzani |
| 2010/0260854 A1 | 10/2010 | Rossi |
| 2010/0286400 A1 | 11/2010 | Urakami |
| 2010/0297226 A1 | 11/2010 | Penhasi |
| 2010/0316709 A1 | 12/2010 | Kurasawa |
| 2011/0045068 A1 | 2/2011 | Valducci |
| 2011/0091563 A1 | 4/2011 | Kurasawa |
| 2011/0135722 A1 | 6/2011 | Criere |
| 2011/0177164 A1 | 7/2011 | Rajan |
| 2011/0177165 A1 | 7/2011 | Gerber |
| 2011/0184024 A1 | 7/2011 | Kwak |
| 2011/0189271 A1 | 8/2011 | Lad |
| 2011/0223244 A1* | 9/2011 | Liversidge ............. A61K 31/00 424/452 |
| 2011/0229562 A1 | 9/2011 | Bar |
| 2011/0229570 A1 | 9/2011 | Sugimoto |
| 2011/0236475 A1 | 9/2011 | Pasha |
| 2011/0281912 A1 | 11/2011 | Winter |
| 2011/0293715 A1 | 12/2011 | Combessis |
| 2011/0311595 A1 | 12/2011 | Berndi |
| 2011/0311631 A1 | 12/2011 | Baer |
| 2012/0004321 A1 | 1/2012 | Hoashi |
| 2012/0027822 A1 | 2/2012 | Politis |
| 2012/0040001 A1 | 2/2012 | Koizumi |
| 2012/0045506 A1 | 2/2012 | Baer |
| 2012/0077888 A1 | 3/2012 | Ramtoola |
| 2012/0082721 A1 | 4/2012 | Buessing |
| 2012/0093926 A1 | 4/2012 | Bodinge |
| 2012/0100093 A1 | 4/2012 | Nonomura |

(56) References Cited

U.S. PATENT DOCUMENTS

| | | | |
|---|---|---|---|
| 2012/0128764 A1 | 5/2012 | Venkatesh |
| 2012/0141584 A1 | 6/2012 | Chauhan |
| 2012/0207825 A1 | 8/2012 | Roy |
| 2012/0219628 A1 | 8/2012 | Lim |
| 2012/0282335 A1 | 11/2012 | Venkatesh |
| 2012/0321702 A1 | 12/2012 | Encina Garcia |
| 2013/0017262 A1 | 1/2013 | Mullen |
| 2013/0090313 A1 | 4/2013 | Marathi |
| 2013/0122090 A1 | 5/2013 | Borude |
| 2013/0189360 A1 | 7/2013 | Sakamoto |
| 2013/0202688 A1 | 8/2013 | Roy |
| 2013/0216617 A1 | 8/2013 | Roy |
| 2013/0217777 A1 | 8/2013 | Kirkorian |
| 2013/0243859 A1 | 9/2013 | Mima |
| 2013/0266658 A1 | 10/2013 | Wei |
| 2013/0273157 A1 | 10/2013 | Ishii |
| 2013/0274243 A1 | 10/2013 | Bagal |
| 2014/0155435 A1 | 6/2014 | Mitchell |
| 2014/0178469 A1 | 6/2014 | Penhasi |
| 2014/0248341 A1 | 9/2014 | Liversidge |
| 2014/0248350 A1 | 9/2014 | Reyes |
| 2014/0255503 A1 | 9/2014 | Sangra Perez |
| 2014/0287051 A1 | 9/2014 | Perrett |
| 2014/0296191 A1 | 10/2014 | Patel |
| 2014/0309219 A1 | 10/2014 | Chang |
| 2014/0314846 A1 | 10/2014 | Penhasi et al. |
| 2014/0343049 A1 | 11/2014 | Toueg |
| 2014/0364513 A1 | 12/2014 | Park |
| 2014/0370104 A1 | 12/2014 | Hall |
| 2014/0377347 A1 | 12/2014 | Vivek |
| 2015/0005232 A1 | 1/2015 | Cheruvallath |
| 2015/0031693 A1 | 1/2015 | McKew |
| 2015/0037423 A1 | 2/2015 | Kurasawa |
| 2015/0038510 A1 | 2/2015 | Lawson |
| 2015/0044303 A1 | 2/2015 | Olmstead |
| 2015/0104512 A1 | 4/2015 | Ognibene |
| 2015/0110880 A1 | 4/2015 | Sekiguchi |
| 2015/0132396 A1 | 5/2015 | Coulter |
| 2015/0216806 A1 | 8/2015 | Borody |
| 2015/0225405 A1 | 8/2015 | Cheruvallath |
| 2015/0225412 A1 | 8/2015 | Brameld |
| 2015/0272889 A1 | 10/2015 | Hoashi |
| 2015/0283085 A1 | 10/2015 | Venkatesh |
| 2015/0297642 A1 | 10/2015 | Borody |
| 2015/0335592 A1 | 11/2015 | Barnscheid |
| 2016/0000721 A1 | 1/2016 | Gupta |
| 2016/0038411 A1 | 2/2016 | Cowles |
| 2016/0074327 A1 | 3/2016 | Naylor |
| 2016/0081977 A1 | 3/2016 | Kock |
| 2016/0089338 A1 | 3/2016 | Kawano |
| 2016/0120809 A1 | 5/2016 | Djordjevic |
| 2016/0128944 A1 | 5/2016 | Chawrai |
| 2016/0128946 A1 | 5/2016 | Humar |
| 2016/0279071 A1 | 9/2016 | Park |
| 2016/0346274 A1 | 12/2016 | Vaka |
| 2016/0354356 A1 | 12/2016 | Moses-Heller |
| 2016/0368908 A1 | 12/2016 | Owens |
| 2017/0042806 A1 | 2/2017 | Moses-Heller |
| 2017/0119660 A1 | 5/2017 | Temtsin-Krayz |
| 2017/0183359 A1 | 6/2017 | Ishida |
| 2017/0298046 A1 | 10/2017 | Soldano |
| 2019/0125676 A1 | 5/2019 | Moses-Heller |

FOREIGN PATENT DOCUMENTS

| | | |
|---|---|---|
| EP | 005129 | 10/1979 |
| EP | 121103 | 10/1984 |
| EP | 124495 | 11/1984 |
| EP | 174726 | 3/1986 |
| EP | 237200 | 9/1987 |
| EP | 237506 | 9/1987 |
| EP | 247983 | 12/1987 |
| EP | 281200 | 2/1988 |
| EP | 313328 | 4/1989 |
| EP | 338861 | 10/1989 |
| EP | 0377518 A2 | 7/1990 |
| EP | 1078628 | 2/1991 |
| EP | 23748 | 4/1991 |
| EP | 444625 | 9/1991 |
| EP | 446961 | 9/1991 |
| EP | 255002 | 5/1992 |
| EP | 496437 | 7/1992 |
| EP | 0519144 A1 | 12/1992 |
| EP | 519365 | 12/1992 |
| EP | 567201 | 10/1993 |
| EP | 408273 | 1/1994 |
| EP | 480729 | 3/1995 |
| EP | 646006 | 4/1995 |
| EP | 589981 | 10/1996 |
| EP | 761212 | 3/1997 |
| EP | 0768082 A1 | 4/1997 |
| EP | 813424 | 7/1997 |
| EP | 795324 | 9/1997 |
| EP | 619825 | 10/1997 |
| EP | 814840 | 1/1998 |
| EP | 828480 | 3/1998 |
| EP | 0567201 B1 | 9/1999 |
| EP | 709087 | 12/1999 |
| EP | 998944 | 5/2000 |
| EP | 661966 | 7/2000 |
| EP | 1043977 | 10/2000 |
| EP | 1051174 | 11/2000 |
| EP | 696921 | 2/2001 |
| EP | 1086694 | 3/2001 |
| EP | 1092434 | 4/2001 |
| EP | 1123700 | 8/2001 |
| EP | 1174136 | 1/2002 |
| EP | 1203580 | 5/2002 |
| EP | 1207809 | 5/2002 |
| EP | 1061920 | 6/2002 |
| EP | 1213015 | 6/2002 |
| EP | 746342 | 8/2002 |
| EP | 1146862 | 4/2003 |
| EP | 1308159 | 5/2003 |
| EP | 1352660 | 10/2003 |
| EP | 1371361 | 12/2003 |
| EP | 1382331 | 1/2004 |
| EP | 1037607 | 2/2004 |
| EP | 1424069 | 6/2004 |
| EP | 1430895 | 6/2004 |
| EP | 1452172 | 9/2004 |
| EP | 1525882 | 4/2005 |
| EP | 1108425 | 6/2005 |
| EP | 1642572 | 4/2006 |
| EP | 1762249 | 3/2007 |
| EP | 1813275 A1 | 8/2007 |
| EP | 1834634 | 9/2007 |
| EP | 1837016 | 9/2007 |
| EP | 1927354 | 6/2008 |
| EP | 2052697 | 4/2009 |
| EP | 2600847 A1 | 6/2013 |
| EP | 2604256 | 6/2013 |
| EP | 2641594 | 9/2013 |
| GB | 2067900 | 8/1981 |
| GB | 2189698 | 11/1987 |
| GB | 2245492 A | 1/1992 |
| IN | 1679/MUM/2010 | 2/2013 |
| JP | 2009256344 A | 11/2009 |
| WO | WO 9116043 | 10/1991 |
| WO | WO 93 01805 | 2/1993 |
| WO | WO 9318755 | 9/1993 |
| WO | WO 9325204 | 12/1993 |
| WO | WO 95 01783 | 1/1995 |
| WO | WO 9520948 | 8/1995 |
| WO | WO 96 01612 | 1/1996 |
| WO | WO 96 01623 | 1/1996 |
| WO | WO 96/01625 | 1/1996 |
| WO | WO 9601624 | 1/1996 |
| WO | WO 96/24375 | 8/1996 |
| WO | WO 96 31213 | 10/1996 |
| WO | WO 97 02020 | 1/1997 |
| WO | WO 9712580 | 4/1997 |
| WO | WO 9712581 | 4/1997 |
| WO | WO 9725030 | 7/1997 |

(56) References Cited

FOREIGN PATENT DOCUMENTS

| WO | WO 9725064 | 7/1997 |
|---|---|---|
| WO | WO 9800114 | 1/1998 |
| WO | 9832426 A1 | 7/1998 |
| WO | WO 98/40069 | 9/1998 |
| WO | WO 9853798 | 12/1998 |
| WO | WO 9853803 | 12/1998 |
| WO | WO 9901112 | 1/1999 |
| WO | WO 9903453 | 1/1999 |
| WO | WO 9913872 | 3/1999 |
| WO | WO 99 25323 | 5/1999 |
| WO | WO 1999027917 | 6/1999 |
| WO | WO 9929320 | 7/1999 |
| WO | WO 9959544 | 11/1999 |
| WO | WO 0012064 | 3/2000 |
| WO | 0018376 A1 | 4/2000 |
| WO | WO 0027366 | 5/2000 |
| WO | WO 0030612 | 6/2000 |
| WO | WO 2000035448 | 6/2000 |
| WO | WO 0059475 | 10/2000 |
| WO | WO 2000078293 | 12/2000 |
| WO | WO 0128558 | 4/2001 |
| WO | WO 01 037808 | 5/2001 |
| WO | WO 01 051050 | 7/2001 |
| WO | WO 0152816 | 7/2001 |
| WO | 0158447 A1 | 8/2001 |
| WO | WO 02 022108 | 3/2002 |
| WO | WO 02 041919 | 5/2002 |
| WO | WO 2002/035991 | 5/2002 |
| WO | WO 02094227 | 11/2002 |
| WO | WO 0072827 | 12/2002 |
| WO | WO 2003007917 A1 | 1/2003 |
| WO | WO 03 009846 | 2/2003 |
| WO | WO 03 061584 | 7/2003 |
| WO | WO 2003086343 | 10/2003 |
| WO | WO 2004052607 | 6/2004 |
| WO | WO 2004098573 | 11/2004 |
| WO | WO 2005034924 | 4/2005 |
| WO | WO 2005058282 | 6/2005 |
| WO | WO 06012634 | 2/2006 |
| WO | WO 2006011159 | 2/2006 |
| WO | WO 2006026829 | 3/2006 |
| WO | 2006058250 A2 | 6/2006 |
| WO | WO 2006067599 | 6/2006 |
| WO | WO 2006116582 | 11/2006 |
| WO | 2007016563 A2 | 2/2007 |
| WO | WO 2007070164 | 6/2007 |
| WO | WO 2007078271 | 7/2007 |
| WO | 2007093642 A2 | 8/2007 |
| WO | WO 2008/047320 | 4/2008 |
| WO | WO 2008140459 | 11/2008 |
| WO | 2009022670 A1 | 2/2009 |
| WO | WO 2009036811 | 3/2009 |
| WO | WO 2009/051022 | 4/2009 |
| WO | WO 2009/071219 | 6/2009 |
| WO | WO 2010018593 | 2/2010 |
| WO | WO 2010022944 | 3/2010 |
| WO | WO 2010034344 | 4/2010 |
| WO | WO 2010056059 | 5/2010 |
| WO | 2010096814 A1 | 8/2010 |
| WO | WO 20100096814 A1 | 8/2010 |
| WO | WO 2010105672 | 9/2010 |
| WO | WO 2010105673 | 9/2010 |
| WO | WO 2010116385 | 10/2010 |
| WO | WO 2010122583 | 10/2010 |
| WO | WO 2011039768 | 4/2011 |
| WO | 2011080502 A2 | 7/2011 |
| WO | WO 2011111027 | 9/2011 |
| WO | WO 2011112709 | 9/2011 |
| WO | 2011140446 A2 | 11/2011 |
| WO | WO 2011144975 | 11/2011 |
| WO | WO 2012017074 | 2/2012 |
| WO | WO 2012022498 | 2/2012 |
| WO | WO 2012/092486 | 7/2012 |
| WO | WO 2013100705 | 7/2013 |
| WO | WO 2013122413 | 8/2013 |
| WO | 2013140120 A1 | 9/2013 |
| WO | WO 2013/141827 | 9/2013 |
| WO | WO 2013156088 | 10/2013 |
| WO | 2013175511 A1 | 11/2013 |
| WO | 2013183497 A1 | 12/2013 |
| WO | 2013186311 A1 | 12/2013 |
| WO | WO 2014/016754 | 1/2014 |
| WO | 2014032741 A1 | 3/2014 |
| WO | 2014032742 A1 | 3/2014 |
| WO | 2014046312 A1 | 3/2014 |
| WO | 2014079922 A1 | 5/2014 |
| WO | WO 2014/136494 | 9/2014 |
| WO | WO 2015/050209 | 4/2015 |
| WO | WO 2015/053227 | 4/2015 |
| WO | WO 2015/193485 | 12/2015 |
| WO | WO 2015/198483 | 12/2015 |
| WO | WO 2016/024493 | 2/2016 |
| WO | 2016092387 A1 | 6/2016 |
| WO | WO 2016/083278 | 6/2016 |
| WO | 2016155786 A1 | 10/2016 |
| WO | WO 2016/174664 | 11/2016 |

OTHER PUBLICATIONS

Fu, Y. Orally Fast Disintegrating Tablets: Developments, Technologies, Taste-Masking and Clinical Studies. Critical Reviews™ in Therapeutic Drug Carrier Systems. 21, 433-475 (2004).

Manivannan et al., Multiparticlate drug delivery systems: Pellet & pelletization technique in Drug Invention Today. 2(5), 233-237 (2010).

United States Pharmacopeial <701>, 2008.

United States Pharmacopeial <1216>, 2016.

United States Pharmacopeial <1217>, 2012.

Jeganathan ("Interpolyelectrolyte Complexes of EudragitTM EPO with Hypromellose Acetate Succinate and EudragitTM EPO with Hypromellose Phthalate as Potential Carriers for Oral Controlled Drug Delivery", AAPS PharmSciTech, vol. 16, No. 4, Aug. 2015).

International Search Report and Written Opinion of the International Searching Authority cited in International Application No. PCT/IL2017/050652 dated Aug. 20, 2017, 13 pages.

Andrews et al., American Journal of Veterinary Research, (1999) vol. 60( 8), pp. 929-931.

Choudhury et al., Indian Journal of Pharmaceutical Sciences, (2010) vol. 72( 4), pp. 491-494.

Colome et al., Journal of Drug Delivery Science and Technology, (2007) vol. 17( 2), pp. 113-118.

Farinha et al., Druge Development and Industrial Pharmacy, (2000) vol. 26(7), pp. 785-790.

Ito et al., International Journal of Pharmaceutics, (2005) vol. 286(1-2), pp. 69-77.

Jedinger et al., European Jornal of Pharmaceutics and Biopharmaceutics, (2014) vol. 87, pp. 217-226.

Kamath et al., International Journal of Pharmacy and Pharmaceutical Sciences, (2012) vol. 4(33), pp. 257-367.

Lehmann et al., Drugs Made in Germany, (1994) vol. 37(2), pp. 53-60.

Raffin, Pharmazie, (2007) vol. 62(5), pp, 361-364.

Shimizu et al, Chemical and pharmaceutical bulletin, (2003) vol. 51(8). pp. 942-947.

Shimizu et al, Chemical and pharmaceutical bulletin, (2003) vol. 51(9). pp. 1029-1035.

Shimizu et al, Chemical and pharmaceutical bulletin, (2003) vol. 51(10). pp. 1121-1127.

Guidance for Industry Orally Disintegrating Tablets. U.S. Department of Health and Human Services; Food and Drug Administration; Center for Drug Evaluation and Research (CDER). Dec. 2008, Chemistry. 6 pages.

US Pharmacopeia <429>; 35(3) Harmonization Stage 6: 429. Light Diffraction Measurement of Particle Size; (2016); 8 pages.

Baldi and Malfertheiner (2003) Lansoprazole fast disintegrating tablet: a new formulation for an established proton pump inhibitor. Digestion 67(1-2): 1-5.

\* cited by examiner

STABLE ORALLY DISINTEGRATING PHARMACEUTICAL COMPOSITIONS

CROSS REFERENCE TO RELATED APPLICATION(S)

This application is a continuation of U.S. application Ser. No. 15/372,917, filed on Dec. 8, 2016 which claims the benefit of U.S. Ser. No. 62/350,916 filed on Jun. 16, 2016, the disclosure of which are incorporated herein in its entirety by reference.

TECHNICAL FIELD

Described herein are orally disintegrating tablets comprising a proton pump inhibitor, methods for making the same, and methods for treating subjects in need thereof. In particular, stable orally disintegrating tablets comprising a plurality of coated units comprising a proton pump inhibitor that demonstrate increased hardness and decreased friability are described.

BACKGROUND

Orally disintegrating tablets (ODT) have become a preferred dosage form for delivering active agents to patients having difficulty swallowing or who experience dysphagia. These patients generally have trouble swallowing large tablets or capsules and may experience reduced compliance to recommended dosing regimens. Thus, these ODT compositions which rapidly disintegrate in the oral cavity provide minimum patient discomfort.

ODTs are typically produced as a single unit form or a multiunit system in which a plurality of particles, each containing an active ingredient, are compressed into a single dosage form. Generally, multiunit systems are preferred for several reasons. For example, following disintegration of the tablet, the plurality of particles distribute over a large area thereby preventing high concentrations of a drug in one location. Further, multiunit systems have a decreased transit time variance, predictable gastric emptying, less absorption variability, and decreased dose dumping risks.

Despite these benefits, the methods for manufacturing ODTs as multiunit system can result in tablets, which are soft, friable, and unsuitable for packaging in typical blister packs or bottles. Thus, designing ODTs as multiunit system, which are stable during manufacturing and storage and also have acceptable friability, remains a challenge.

Additionally, many active pharmaceutical ingredients are susceptible to highly acidic environments. For example, proton pump inhibitors which most commonly are benzimidazole derivatives are susceptible to degradation and transformation in acidic media. These types of active ingredients should be protected both during storage and during their passage through the acidic environment of the stomach. Therefore, multiunit ODTs having acid-labile active pharmaceutical ingredients are typically formulated with enteric coatings, which are applied to the particles. However, stability problems can arise when particles coated with enteric coatings are compressed into a tablet. Typically, enteric coatings suffer from increased brittleness, which causes cracking during the compression tableting process. Plasticizers can aid in reducing cracking of the coatings, however, when used in excess, they may decrease the effectiveness of the enteric coat.

There have been known approaches to formulate and manufacture ODTs see, for example Fu, Y. Orally Fast Disintegrating Tablets: Developments, Technologies, Taste masking and Clinical Studies. *Critical Reviews™ in Therapeutic Drug Carrier Systems.* 21, 433-475. Many of these approaches are characterized by several advantages including quick disintegration in the oral cavity. However, they are most often accompanied by high levels of friability and/or sensitivity to humidity. Alternatively, the hitherto known compositions may be formulated to have increased stability and hardness, but as a result suffer from longer disintegration times. Thus, there remains a need for ODT compositions, which demonstrate fast disintegration times, reduced taste of bitter active ingredients, and high stability (e.g., low friability).

BRIEF SUMMARY

The pharmaceutical compositions described herein comprise an orally disintegrating tablet that includes one or more active pharmaceutical ingredients. In some embodiments, the active pharmaceutical ingredient is a proton pump inhibitor. In other embodiments, the active pharmaceutical ingredient is an acid-labile active ingredient, such as a benzimidazole derivative proton pump inhibitor. The orally disintegrating tablets described herein disintegrate rapidly in the oral cavity and demonstrate high stability and low friability.

Provided herein is a compressed orally disintegrating tablet comprising a disintegrant and a plurality of units comprising: i) a plurality of cores comprising a therapeutically effective amount of a proton pump inhibitor; ii) an enteric coating over the cores; and iii) a coating comprising a reverse enteric polymer over the enteric coating; wherein a friability of the compressed tablet is about 0.75% or less when about 10 kN to about 50 kN of a compression force is applied during manufacturing of the tablet. In one embodiment, each core comprises an inert seed coated with an active ingredient coating comprising a proton pump inhibitor. In another embodiment, the proton pump inhibitor comprises omeprazole, lansoprazole, pantoprazole, rabeprazole, tenatoprazole, ilaprazole or a combination thereof. Each possibility represents a separate embodiment. In yet another embodiment, the inert seed comprises a granule, a pellet, a bead, or a powder. Each possibility represents a separate embodiment.

In some embodiments, each unit further comprises a subcoating between the core and the enteric coating. In particular embodiments, the subcoating applied to the core comprises one or more of hydroxypropyl methylcellulose, hydroxypropyl cellulose, polyvinylpyrrolidone, polyethylene glycol, polyvinyl alcohol or a mixture or combination thereof, with each possibility representing a separate embodiment.

In certain embodiments, the enteric coating applied to the core or to the subcoating comprises one or more of cellulose acetate phthalate (CAP), hydroxypropyl methylcellulose phthalate (HPMCP), hydroxypropyl methylcellulose acetate succinate (HPMCAS), polyvinyl acetate phthalate, cellulose acetate trimellitate, shellac, polymethacrylic acid, polymethyl methacrylate, polyethyl methacrylate, polyethyl acrylate or a mixture or combination thereof, with each possibility representing a separate embodiment.

In further embodiments, the coating comprising a reverse enteric polymer comprises a (meth)acrylate polymer or copolymer. In another embodiment, the coating comprising a reverse enteric polymer comprises a methyl methacrylate-butyl methacrylate-dimethylaminoethyl methacrylate copolymer. In further embodiments, the coating comprising a reverse enteric polymer is in a range of from about 0.5% to about 20% (w/w) of a total weight of the tablet.

In other embodiments, the orally disintegrating tablet comprises a disintegrant comprising one or more of crospovidone, croscarmellose sodium, a cellulose derivative, cross-linked derivatives of starch, pregelatinized starch, crosslinked sodium carboxymethylcellulose, low substituted hydroxypropylcellulose or a mixture or combination thereof. Each possibility represents a separate embodiment.

In additional embodiments, the orally disintegrating tablet further comprises one or more pharmaceutically acceptable excipients selected from the group consisting of a binder, a filler, a diluent, a surfactant, a glidant, a lubricant, a plasticizer, an anti-tacking agent, an alkaline substance, a tonicity enhancing agent, a wetting agent, a buffering substance, a preservative, a flavoring agent, an opacifier, a colorant, an anti-oxidant or a mixture or combination thereof. Each possibility represents a separate embodiment.

In various embodiments, the orally disintegrating tablet has a hardness of about 20 N to about 100 N. In other embodiments, the orally disintegrating tablet substantially disintegrates in an oral cavity of a subject in need thereof within less than about 60 seconds after administration.

Another embodiment described herein is a compressed orally disintegrating tablet comprising a disintegrant in an amount of about 2% to about 25% by weight of a total tablet weight; a plurality of units comprising: i) a plurality of cores comprising a therapeutically effective amount of a proton pump inhibitor, the plurality of cores in an amount of about 5% to about 25% by weight of a total tablet weight, ii) an enteric coating in an amount of about 10% to about 30% by weight of a total tablet weight; iii) a coating comprising a reverse enteric polymer in an amount of about 5% to about 15% by weight of a total tablet weight; and optionally one or more additional excipients selected from the group consisting of a binder, a filler, a diluent, a surfactant, a glidant, a lubricant, a plasticizer, an anti-tacking agent, an alkaline substance, a tonicity enhancing agent, a wetting agent, a buffering substance, a preservative, a flavoring agent, an opacifier, a colorant, an anti-oxidant or a mixture or combination thereof in an amount of not more than about 50% by weight of a total tablet weight, wherein the weight of all components add to 100% (w/w). In one embodiment, the plurality of units further comprises a subcoating between the cores and the enteric coating in an amount of about 2% to about 15% by weight of a total tablet weight.

According to another aspect, there is provided a process of manufacturing the compressed orally disintegrating tablet described herein, the process comprising: a) generating a plurality of cores comprising a therapeutically effective amount of a proton pump inhibitor; b) applying a solution or dispersion comprising an enteric polymer to the plurality of cores of step (a) thereby obtaining a plurality of enteric coated cores; c) applying a solution or dispersion comprising a reverse enteric polymer to the enteric coated cores of step (b) thereby obtaining a plurality of units; d) mixing the plurality of units with at least one tablet excipient comprising a disintegrant thereby obtaining a blend; and e) compressing the blend of step (d) thereby obtaining the compressed orally disintegrating tablet. In one embodiment, the step of generating a plurality of cores comprises applying a solution or dispersion comprising a therapeutically effective amount of a proton pump inhibitor to a plurality of inert seeds.

In another embodiment, the process for manufacturing the compressed orally disintegrating tablet described herein further comprises an additional step prior to the step b) comprising: a1) applying a solution or dispersion comprising at least one of hydroxypropyl methylcellulose, hydroxypropyl cellulose, polyvinylpyrrolidone, polyethylene glycol, polyvinyl alcohol or a mixture or combination thereof to the plurality of cores of step (a) thereby obtaining a subcoating between the cores and the enteric coating.

Another embodiment described herein is an orally disintegrating tablet prepared by the process of manufacturing described herein.

Another embodiment is an orally disintegrating tablet described herein for use in treating a gastric disorder. In some embodiments, the gastric disorder comprises gastric reflux, gastroesophageal reflux disease, laryngopharyngeal reflux, laryngitis, dyspepsia, Barrett's esophagus, eosinophilic esophagitis, gastritis, gastrinomas, Zollinger-Ellison syndrome, peptic ulcers, or excessive *Helicobacter pylori* or combinations thereof. Each possibility represents a separate embodiment.

In another embodiment, there is provided a method of treating a subject having a gastric disorder comprising administering to the subject a compressed orally disintegrating tablet described herein. In one aspect, the gastric disorder comprises gastric reflux, gastroesophageal reflux disease, laryngopharyngeal reflux, laryngitis, dyspepsia, Barrett's esophagus, eosinophilic esophagitis, gastritis, gastrinomas, Zollinger-Ellison syndrome, peptic ulcers, or excessive *Helicobacter pylori* or combinations thereof. Each possibility represents a separate embodiment.

According to another aspect described herein, there is provided a method for increasing a compressibility of a compressed orally disintegrating tablet comprising a disintegrant and a plurality of units comprising: i) a plurality of cores comprising a therapeutically effective amount of a proton pump inhibitor; and ii) an enteric coating over the cores; the method comprising the step of applying a coating comprising a reverse enteric polymer over the enteric coated cores. In certain embodiments, the increased compressibility comprises one or more of a decreased friability or an increased hardness compared to a compressed orally disintegrating tablet not comprising a coating comprising a reverse enteric polymer when a substantially identical compression force is applied during manufacturing of the tablet. In one embodiment, the decreased friability is about 0.75% or less when about 10 kN to about 50 kN of compression force is applied during manufacturing of the tablet. In another embodiment, the increased hardness is about 20 N to about 100 N when about 10 kN to about 50 kN of compression force is applied during manufacturing of the tablet.

DETAILED DESCRIPTION

The following paragraphs describe in more detail the embodiments of the invention described herein. The following embodiments are not meant to limit the invention or narrow the scope thereof, as it will be readily apparent to one of ordinary skill in the art that suitable modifications and adaptations may be made without departing from the scope of the invention, embodiments, or specific aspects described herein. All patents and publications cited herein are incorporated by reference in their entirety.

Described herein are rapidly disintegrating oral pharmaceutical compositions comprising one or more active pharmaceutical ingredients. The pharmaceutical composition is in the form of a compressed multiunit orally disintegrating tablet (ODT). The term "orally disintegrating tablet" as used herein refers to a tablet which substantially disintegrates in an oral cavity of a subject in need thereof within less than about 60 seconds after administration. The disintegration can be measured in vitro using e.g. the USP <701> Disintegration Test. Additionally, "orally disintegrating tablet" can refer to a loss of structural integrity of the tablet following administration to the buccal cavity of a subject when in contact with the mucosal tissue of the tongue, cheek, and/or mouth. The orally disintegrating tablet is typically placed on the tongue (lingual administration) which stimulates saliva generation and enhances disintegration of the composition. Following disintegration, a suspension of undissolved particles in saliva is typically formed. The particles can then be swallowed, usually without water or other fluids, allowing for absorption of the active pharmaceutical ingredient in the GI tract, generally in the upper intestine. In some embodiments, the active pharmaceutical ingredient comprises a proton pump inhibitor, such as a benzimidazole derivative. In certain embodiments, the orally disintegrating tablet comprises a plurality of units comprising a plurality of cores comprising the one or more active pharmaceutical ingredients. In some embodiments, the plurality of cores is coated with an enteric coating which is over-coated with a coating comprising a reverse enteric polymer. In various embodiments, the units further comprise a subcoating between the cores comprising a therapeutically effective amount of a proton pump inhibitor and the enteric coating. The orally disintegrating tablet further comprises a disintegrant. Optionally, the orally disintegrating tablet further comprises other pharmaceutically acceptable tableting excipients in addition to the disintegrant.

It has been surprisingly found that the addition of a coating comprising a reverse enteric polymer to the plurality of enteric coated cores reduces the friability of the orally disintegrating tablets described herein compared to an orally disintegrating tablet not having a reverse enteric polymer coating. It is believed that this coating layer functions as a compressibility-aid coating, which improves the compressibility of the entire composition. Furthermore, this coating, which is applied as an over-coating layer, may also demonstrate taste masking properties. Thus, it is contemplated that the coating layer comprising a reverse enteric polymer has dual functionality in that it increases the compressibility of the entire tablet composition while affording substantially complete masking of the proton pump inhibitor bitter taste. These advantages were found to be achieved even with a thin coating layer. The resulting compressed orally disintegrating tablet demonstrates good friability and fast disintegration times. Thus, because this coating improves the compressibility of the composition, it can be applied in instances where taste masking is not required.

Plurality of Units

The orally disintegrating tablets described herein comprise a plurality of coated units comprising a plurality of cores comprising a therapeutically effective amount of an active pharmaceutical ingredient. Therefore, each unit within the total plurality of units comprises a core comprising an active pharmaceutical ingredient. These cores are further coated with coating layers comprising an enteric coating layer and a coating comprising a reverse enteric polymer. The enteric coating layer modulates the release characteristics of the active ingredient to afford its delayed release, and the coating comprising a reverse enteric polymer affords the increase in tablet strength and reduced friability, and in some embodiments provides for a taste masking effect for bitter active ingredients.

Plurality of Cores

According to certain embodiments, the plurality of units comprises a plurality of cores comprising a therapeutically effective amount of an active pharmaceutical ingredient. In some embodiments, the active pharmaceutical ingredient is a proton pump inhibitor. Proton pump inhibitors or PPIs refer to any pharmacologically active ingredient which inhibits the hydrogen potassium adenosine triphosphatase enzyme system (e.g., the $H^+/K^+$ ATPase) of gastric parietal cells. As described herein, proton pump inhibitors may include benzimidazole derivatives, imidazopyridine derivatives or a potassium-competitive inhibitor and mixtures thereof. Each possibility represents a separate embodiment. The inhibition by the proton pump inhibitor may be irreversible or reversible.

Exemplary and non-limiting benzimidazole derivative proton pump inhibitors include omeprazole, esomeprazole, lansoprazole, dexlansoprazole, pantoprazole, rabeprazole, ilaprazole and AGN201904; each possibility represents a separate embodiment. Exemplary imidazopyridine derivative proton pump inhibitors include, but are not limited to, tenatoprazole; and exemplary potassium-competitive inhibitors include, but are not limited to, revaprazan. See also, U.S. Pat. No. 5,753,265, which is incorporated by reference herein for its teachings of proton pump inhibitors.

The proton pump inhibitor active ingredient also comprises alkali metal salts thereof such as, sodium or potassium salts, and alkaline earth metal salts thereof such as, for example, calcium and magnesium salts. Each possibility represents a separate embodiment. The proton pump inhibitor may also be in the form of pharmaceutically acceptable uncharged or charged molecules, molecular complexes, solvates, or anhydrates thereof, and, if relevant, single isomers, enantiomers, racemates, or mixtures thereof. In addition, the proton pump inhibitor may be in any of its crystalline, polymorph, semi-crystalline, amorphous or polyamorphous forms, or mixtures thereof. Each possibility represents a separate embodiment.

In some embodiments, the proton pump inhibitor is in a weight percent ratio to the total compressed tablet of about 1:40 to about 1:2, including all iterations of ratios within the specified range. In other embodiments, the weight percent ratio of the proton pump inhibitor to the total compressed tablet is about 1:30 to about 1:2. In yet other embodiments, the weight percent ratio of the proton pump inhibitor to the total compressed tablet is about 1:20 to about 1:2. In one embodiment, the weight percent ratio of the proton pump inhibitor to the total compressed tablet is about 1:17.

In certain embodiments, the orally disintegrating tablet comprises a plurality of units comprising multiple cores comprising a therapeutically effective amount of one or more proton pump inhibitors such as, but not limited to, omeprazole. In one embodiment, each core is in a form such as, but not limited to, a granule, a pellet, a bead or a powder. Each possibility represents a separate embodiment. The cores typically comprise one or more pharmaceutically acceptable excipients (e.g. a filler, a binder, an alkalizing agent etc.) and a proton pump inhibitor and may be generated through methods well-known in the pharmaceutical arts, for example, dry or wet granulation, extrusion or spheronization, see also, Remington, J. P.; Beringer, P. *Remington: The Science and Practice of Pharmacy*; Lippincott Williams & Wilkins: Philadelphia, 2006.

For example, these types of cores, also referred to as "active cores" may be formed by compressing the active ingredient with one or more pharmaceutically acceptable excipients such as a filler (e.g. lactose), a binder (e.g., polyvinylpyrrolidone) and/or an alkalizing agent (e.g., sodium stearate) etc. Alternatively, the active core may be prepared by mixing the proton pump inhibitor with one or more pharmaceutically acceptable excipients and forming a plurality of cores (e.g., granules, spheroids etc.) through granulation, extrusion or spheronization techniques. In accordance with these embodiments, the proton pump inhibitor is embedded in a matrix of one or more pharmaceutically acceptable excipients.

In some embodiments, each core within the plurality of cores comprises an inert seed coated with an active ingredient coating layer comprising one or more active pharmaceutical ingredients. The active ingredient coating layer applied to the inert seed may include one or more pharmaceutically acceptable excipients, such as, but not limited to, a binder, an alkalizing agent, and a filler. Each possibility represents a separate embodiment. Suitable inert seeds may be any of a bead (e.g., a sugar bead), a pellet (e.g., a microcrystalline cellulose (MCC) pellet), a granule, a powder or other seeds known in the art, which are coated with one or more active ingredients (e.g., a proton pump inhibitor). Exemplary and non-limiting inert seeds onto which the drug-containing layer is applied are usually comprised of sugars, starch or cellulosic materials or combinations thereof, for example sugar derivatives such as lactose, sucrose, hydrolyzed starch (maltodextrins) or celluloses or mixtures thereof. In one embodiment, the inert seeds comprise nonpareils comprising a blend of starch and sugar. The nonpareils, also called sugar spheres, typically comprise spheres composed of sucrose and starch (for example, maize starch). In another embodiment, the inert seeds comprise microcrystalline cellulose particles. Other types of seeds may also be used. Suitable commercially available inert seeds include, for example, SUGLETS® from Colorcon. The shape of the seed may be spherical or a semi-spherical in shape. See, for example, Manivannan et al., *Drug Invention Today* 2(5) 233-237 (2010) and U.S. Pat. Nos. 3,119,742; 4,871,549; 5,328,697; 5,725,886; and 6,558,704; and PCT International Patent Publication No. WO 2002/035991.

Thus, in some embodiments, the plurality of cores comprises active cores comprising an active pharmaceutical ingredient and one or more pharmaceutically acceptable excipients, such as a filler, binder and/or an alkalizing agent. In other embodiments, the plurality of cores comprises inert seeds coated with an active ingredient coating layer that includes the active pharmaceutical ingredient and optionally one or more additional pharmaceutically acceptable excipients, such as a filler, binder and/or an alkalizing agent. In further embodiments, the plurality of cores comprise a first portion of a proton pump inhibitor in an active core as described herein which are further coated with a second portion of a proton pump inhibitor so that the combination of the first and second portions constitute a therapeutically effective amount of the proton pump inhibitor.

In some embodiments, the cores comprising an active pharmaceutical ingredient comprise inert seeds in an amount of about 15% to about 75% by weight of the total mass of the plurality of cores, including each integer within the specified range. In other embodiments, the inert seeds are in an amount of about 20% to about 70% by weight of the total mass of the plurality of cores, including each integer within the specified range. In yet other embodiments, the inert seeds are in an amount of about 25% to about 65% by weight of the total mass of the plurality of cores, including each integer within the specified range. In certain embodiments, the inert seeds are in an amount of about 15%, about 20%, about 25%, about 30%, about 35%, about 40%, about 45%, about 50%, about 55%, about 60%, about 65%, about 70%, or about 75% by weight of the total mass of the plurality of cores, with each possibility representing a separate embodiment. In one embodiment, the inert seeds comprise sugar spheres.

In some embodiments, the active ingredient is in an amount of about 5% to about 85% by weight of the total mass of the plurality of cores, including each integer within the specified range. In one embodiment, the active ingredient is in an amount of about 10% to about 80% by weight of the total mass of the plurality of cores, including each integer within the specified range. In another embodiment, the active ingredient is in an amount of about 15% to about 70% by weight of the total mass of the plurality of cores, including each integer within the specified range. In other embodiments, the active ingredient is in an amount of about 20% to about 60% by weight of the total mass of the plurality of cores, including each integer within the specified range. In further embodiments, the active ingredient is in an amount of about 30% to about 50% by weight of the total mass of the plurality of cores, including each integer within the specified range. In certain embodiments, the active ingredient is in an amount of about 5%, about 10%, about 15%, about 20%, about 25%, about 30%, about 35%, about 40%, about 45%, about 50%, about 55%, about 60%, about 65%, about 70%, about 75%, about 80%, or about 85% by weight of the total mass of the plurality of cores, with each possibility representing a separate embodiment. In several embodiments, the active ingredient comprises a proton pump inhibitor such as omeprazole or a pharmaceutically acceptable salt thereof.

In some embodiments, the plurality of cores comprising an active pharmaceutical ingredient further comprises a binder in an amount of about 5% to about 40% by weight of the total mass of the plurality of cores, including each integer within the specified range. In several embodiments, the binder is in an amount of about 10% to about 35% by weight of the total mass of the plurality of cores, including each integer within the specified range. In other embodiments, the binder is in an amount of about 15% to about 30% by weight of the total mass of the plurality of cores, including each integer within the specified range. In additional embodiments, the binder is in an amount of about 5%, about 10%, about 15%, about 20%, about 25%, about 30%, about 35%, or about 40% by weight of total mass of the plurality of cores, with each possibility representing a separate embodiment. In certain embodiments, the binder comprises hydroxypropyl methyl cellulose (HPMC). In other embodiment, the binder comprises povidone or copovidone.

In some embodiments, the plurality of cores comprising an active pharmaceutical ingredient further comprises an alkalizing agent in an amount of about 0.2% to about 10% by weight of the total mass of the plurality of cores, including each integer within the specified range. In one embodiment, the alkalizing agent is in an amount of about 0.3% to about 5% by weight of the total mass of the plurality of cores, including each integer within the specified range. In another embodiment, the alkalizing agent is in an amount of about 0.4% to about 2% by weight of the total mass of the plurality of cores, including each integer within the specified range. In certain embodiments, the alkalizing agent is in an amount of about 0.2%, about 0.4%, about 0.8%, about 1%, about 2%, about 4%, about 6%, about 8%, or about 10% by weight of the total mass of the plurality of cores, with each possibility representing a separate embodiment. In one embodiment, the alkalizing agent comprises sodium stearate. In another embodiment, the alkalizing agent comprises meglumine.

In some embodiments, the plurality of cores are in an amount of about 5% to about 50% of the total orally disintegrating tablet composition mass, including each integer within the specified range. The total orally disintegrating tablet composition mass, as used herein, refers to the weight of the plurality of units, including the active ingredient and all applied coatings in addition to the tablet matrix and all other tablet excipients. In other embodiments, the plurality of cores are in an amount of about 5% to about 40% of the total orally disintegrating tablet composition mass, including each integer within the specified range. In yet other embodiments, the plurality of cores are in an amount of about 5% to about 30% of the total orally disintegrating tablet composition mass, including each integer within the specified range. In further embodiments, the plurality of cores are in an amount of about 5% to about 25% of the total orally disintegrating tablet composition mass, including each integer within the specified range. In certain embodiments, the plurality of cores are in an amount of about 5%, about 10%, about 15%, about 20%, about 25%, about 30%, about 35%, about 40%, about 45%, or about 50% of the total orally disintegrating tablet composition mass, with each possibility representing a separate embodiment.

Subcoating

In some embodiments, the plurality of cores comprising an active pharmaceutical ingredient is coated with a subcoating layer. This subcoating layer may prevent an interaction between the enteric coating layer having free carboxyl groups and the core that comprises one or more active pharmaceutical ingredients which are typically benzimidazole derivatives known to be acid-labile. The subcoating layer is designed to afford physical separation between the alkaline core containing one or more proton pump inhibitors and the acidic enteric coating. In certain embodiments, the subcoating layer comprises one or more of a binder, a filler, and an anti-tacking agent, with each possibility representing a separate embodiment.

In some embodiments, the subcoating layer comprises a binder in an amount of about 20% to about 75% of the total subcoating layer mass, including each integer within the specified range. In other embodiments, the binder is in an amount of about 20% to about 65% of the total subcoating layer mass, including each integer within the specified range. In yet other embodiments, the binder is in an amount of about 30% to about 60% of the total subcoating layer mass, including each integer within the specified range. In certain embodiments, the binder is in an amount of about 20%, about 25%, about 30%, about 35%, about 40%, about 45%, about 50%, about 55%, about 60%, about 65%, about 70%, or about 75% of the total subcoating layer mass, with each possibility representing a separate embodiment. In one embodiment, the binder comprises hydroxypropylmethyl cellulose. In other embodiment, the binder comprises povidone or copovidone.

In some embodiments, the subcoating layer comprises a filler in an amount of about 15% to about 50% of the total subcoating layer mass, including each integer within the specified range. In one embodiment, the filler is in an amount of about 25% to about 50% of the total subcoating layer mass, including each integer within the specified range. In another embodiment, the filler is in an amount of about 25% to about 45% of the total subcoating layer mass, including each integer within the specified range. In yet another embodiment, the filler is in an amount of about 15%, about 20%, about 25%, about 30%, about 35%, about 40%, about 45%, or about 50% of the total subcoating layer mass, with each possibility representing a separate embodiment. In some embodiments, the filler comprises mannitol.

In some embodiments, the subcoating layer comprises an anti-tacking agent in an amount of about 1% to about 12% of the total subcoating layer mass, including each integer within the specified range. In other embodiments, the anti-tacking agent is in an amount of about 2% to about 10% of the total subcoating layer mass, including each integer within the specified range. In yet other embodiments, the anti-tacking agent is in an amount of about 3% to about 9% of the total subcoating layer mass, including each integer within the specified range. In further embodiments, the anti-tacking agent is in an amount of about 1%, about 3%, about 6%, about 9%, or about 12% of the total subcoating layer mass, with each possibility representing a separate embodiment. In certain embodiments, the anti-tacking agent comprises talc.

Enteric Coating

In some embodiments, the plurality of units comprises an enteric coating, which protects the active ingredients (e.g., a proton pump inhibitor) from the acidic environment of the stomach. The enteric coating includes one or more enteric polymers and optionally other pharmaceutically acceptable excipients, such as a plasticizer, a glidant, and an opacifier described herein. In some embodiments, the enteric coating is applied directly over the cores comprising an active ingredient. In other embodiments, the enteric coating is applied over the subcoating layer, which is over the cores. Generally, enteric coatings include pH dependent polymers. These polymers are typically characterized by increase in permeability at pH values of above pH 5.0 (e.g., intestinal fluid) while remaining insoluble at low pH values, such as those found in the environment of the stomach.

Exemplary and non-limiting enteric polymers include acrylic and methacrylate acid copolymers, cellulose acetate phthalate (CAP), cellulose acetate butyrate, hydroxypropylmethylcellulose phthalate (HPMCP), hydroxypropyl methylcellulose acetate succinate (HPMCAS), polyvinyl acetate phthalate, cellulose acetate trimellitate, alginic acid salts, such as sodium or potassium alginate, and shellac. Each possibility represents a separate embodiment. Acrylic and methacrylate acid copolymers are anionic copolymers based on (meth)acrylic acid and alkyl (meth)acrylate, such as, but not limited to, polymethacrylic acid, polymethyl methacrylate, polyethyl methacrylate, and polyethyl acrylate among others. Commercial acrylic and methacrylate acid copolymers are available under the trade name EUDRAGIT® (Evonik Industries AG, Essen, Germany) and are typically provided as powder or aqueous dispersions, including, but not limited to, EUDRAGIT® L 30 D-55; EUDRAGIT® L 100-55; EUDRAGIT® L 100; EUDRAGIT® L 12.5; EUDRAGIT® NE 40 D, EUDRAGIT® RL 100, EUDRAGIT® S 100; EUDRAGIT® S 12.5; EUDRAGIT® FS 30 D; EUDRAGIT® RL PO; EUDRAGIT® RL 12.5, EUDRAGIT® RL 30 D; EUDRAGIT® RS 100; EUDRAGIT® RS PO; EUDRAGIT® RS 30 D; EUDRAGIT® RS 12.5; EUDRAGIT® NE 30 D; EUDRAGIT® NM 30 D; or combinations and mixtures thereof. In certain embodiments, the enteric coating comprises hydroxypropylmethylcellulose phthalate (HPMCP).

In some embodiments, the enteric polymer is in an amount of about 50% to about 100% of the total enteric coating layer mass, including each integer within the specified range. In other embodiments, the enteric polymer is in an amount of about 55% to about 100% of the total enteric coating layer mass, including each integer within the specified range. In yet other embodiments, the enteric polymer is in an amount of about 60% to about 100% of the total enteric coating layer mass, including each integer within the specified range. In further embodiments, the enteric polymer is in an amount of about 60% to about 90% of the total enteric coating layer mass, including each integer within the specified range. In additional embodiments, the enteric polymer is in an amount of about 60% to about 85% of the total enteric coating layer mass, including each integer within the specified range. In certain embodiments, the enteric polymer is in an amount of about 50%, about 55%, about 60%, about 65%, about 70%, about 75%, about 80%, about 85%, about 90%, about 95%, or even about 100% of the total enteric coating layer mass, with each possibility representing a separate embodiment.

In some embodiments, the enteric coating layer further comprises one or more plasticizers. Plasticizers are known to increase the flexibility of the coating and help prevent or reduce cracking of the enteric coat upon compression. Further, plasticizers may also increase the adhesion of the enteric coating polymer chains. Exemplary and non-limiting plasticizers include glycerol, polyethylene glycol and derivatives thereof, citric acid esters, such as triethyl citrate, and tributyl citrate, fatty alcohol derivatives such as cetyl alcohol, stearyl alcohol or phthalate derivatives, such as diethyl phthalate, dipropyl phthalate, dibutyl phthalate, dibutyl sebacate, or dioctyl phthalate or a mixture or combination thereof. Each possibility represents a separate embodiment. In certain embodiments, the plasticizer comprises triethyl citrate, cetyl alcohol or a mixture thereof.

In some embodiments, the one or more plasticizers are in an amount of about 5% to about 50% of the total enteric coating layer mass, including each integer within the specified range. In other embodiments, the one or more plasticizers are in an amount of about 5% to about 40% of the total enteric coating layer mass, including each integer within the specified range. In yet other embodiments, the one or more plasticizers are in an amount of about 5% to about 30% of the total enteric coating layer mass, including each integer within the specified range. In further embodiments, the one or more plasticizers are in an amount of about 5% to about 20% of the total enteric coating layer mass, including each integer within the specified range. In additional embodiments, the one or more plasticizers are in an amount of about 15% to about 25% of the total enteric coating layer mass, including each integer within the specified range. In certain embodiments, the one or more plasticizers are in an amount of about 5%, about 10%, about 15%, about 20%, about 25%, about 30%, about 35%, about 40%, about 45%, or about 50% of the total enteric coating layer mass, with each possibility representing a separate embodiment.

In some embodiments, the weight of the enteric coating on the plurality of cores is about 10% to about 40% of the total orally disintegrating tablet composition mass, including each integer within the specified range. In one embodiment, the weight of the enteric coating on the plurality of cores is about 10% to about 30% of the total orally disintegrating tablet composition mass, including each integer within the specified range. In other embodiments, the weight of the enteric coating on the plurality of cores is about 10%, about 15%, about 20%, about 25%, about 30%, about 35%, or about 40% by weight of the total orally disintegrating tablet composition mass, with each possibility representing a separate embodiment.

Coating Comprising a Reverse Enteric Polymer

In some embodiments, the enteric coated cores are overcoated with a coating layer comprising a reverse enteric polymer. This coating was surprisingly found to increase the compressibility of the orally disintegrating tablets described herein. In particular, coatings having a reverse enteric polymer were found to reduce the friability and increase the overall stability of the orally disintegrating tablets described herein while affording adequate release profile of the active pharmaceutical ingredient. In certain embodiments, the coating layer comprising a reverse enteric polymer is an over-coating that is an outermost coating layer which is layered on the penultimate coating of the coated core (e.g., over the enteric coating layer).

As used herein and in the appended claims, the term "reverse enteric polymer" refers to pH sensitive polymers, which are insoluble at pH values greater than those found in the stomach i.e. at pH values greater than 5.0 while being soluble at acidic pH values. Suitable reverse enteric polymers are thus insoluble in the oral cavity and soluble in the stomach.

In some embodiments, the reverse enteric polymer is a copolymer of hydrophobic monomers and/or basic monomers; non-limiting examples of such reverse enteric polymers are described in U.S. Patent Application No. 2006/0134054.

In certain embodiments, the monomer is an acrylic or a methacrylic acid ester comprising, but not limited to, methyl (meth)acrylate, benzyl (meth)acrylate, dodecyl (meth)acrylate, octyl (meth)acrylate, cyclohexyl (meth)acrylate, phenyl (meth)acrylate, tertiary butyl (meth)acrylate, butyl (meth)acrylate, ethyl hexyl (meth)acrylate, propyl (meth)acrylate, or combinations thereof. Each possibility represents a separate embodiment.

In other embodiments, the monomer is a substituted acrylic or a methacrylic acid ester comprising, but not limited to, dimethyl amino ethyl (meth)acrylate, diethyl amino ethyl (meth)acrylate, piperidine ethyl (meth)acrylate, tertbutyl amino ethyl (meth)acrylate, or combinations thereof. Each possibility represents a separate embodiment.

In various embodiments, the monomer is an alkenyl pyridine comprising, but not limited to, vinyl pyridine, vinyl picoline, isopropenyl pyridine, or combinations thereof. In yet additional embodiments, the monomer comprises vinyl quinolines, aminoalkyl vinyl ethers, amino ethyl styrenes or allylic amines or combinations thereof. Each possibility represents a separate embodiment.

In one embodiment, the reverse enteric polymer includes a (meth)acrylate polymer or copolymer, such as acrylate and methacrylate copolymers having primary, secondary or tertiary amino groups or quaternary ammonium groups. These reverse enteric polymers are commercially available as EUDRAGIT® E 100; EUDRAGIT® E 12.5; EUDRAGIT® EPO; or EUDRAGIT® RL 100 (Evonic Industries). Each possibility represents a separate embodiment. Currently preferred reverse enteric polymer is a methyl methacrylate-butyl methacrylate-dimethylaminoethyl methacrylate copolymer (e.g., poly(butyl methacrylate-co-(2-dimethylaminoethyl) methacrylate-co-methyl methacrylate) 1:2:1).

In some embodiments, the reverse enteric polymer coating layer further comprises additional polymers. The additional polymers that may be present in this coating layer include, but are not limited to, ethyl cellulose, polyvinyl acetate (PVA), cellulose acetate (CA), and cellulose acetate butyrate (CAB). Each possibility represents a separate embodiment.

In some embodiments, this coating layer further provides taste masking properties, which may reduce the taste sensation of active ingredients characterized by bitter or unpleasant taste. However, this coating layer can also be applied where a taste-masking effect is not required due to its unexpected effect of increasing the compressibility of the orally disintegrating tablets described herein.

In some embodiments, the coating comprising a reverse enteric polymer further comprises one or more pharmaceutically acceptable excipients, such as a glidant or colorant described herein. In additional embodiments, the coating comprising a reverse enteric polymer further comprises one or more of carboxymethylcellulose, polyvinyl alcohol and polyethylene glycol copolymer (e.g., Kollicoat® IR). Each possibility represents a separate embodiment.

In some embodiments, the reverse enteric polymer is in an amount of about 30% to about 100% of the total reverse enteric coating layer mass, including each integer within the specified range. In other embodiments, the reverse enteric polymer is in an amount of about 40% to about 100% of the total reverse enteric coating layer mass, including each integer within the specified range. In yet other embodiments, the reverse enteric polymer is in an amount of about 50% to about 100% of the total reverse enteric coating layer mass, including each integer within the specified range. In further embodiments, the reverse enteric polymer is in an amount of about 60% to about 100% of the total reverse enteric coating layer mass, including each integer within the specified range. In additional embodiments, the reverse enteric polymer is in an amount of about 70% to about 100% of the total reverse enteric coating layer mass, including each integer within the specified range. In yet other embodiments, the reverse enteric polymer is in an amount of at least 80% of the total reverse enteric coating layer mass. In further embodiments, the reverse enteric polymer is in an amount of at least 90% of the total reverse enteric coating layer mass. In other embodiments, the reverse enteric polymer is in an amount of at least 95% of the total reverse enteric coating layer mass. In certain embodiments, the reverse enteric polymer is in an amount of about 30%, about 35%, about 40%, about 45%, about 50%, about 55%, about 60%, about 65%, about 70%, about 75%, about 80%, about 85%, about 90%, about 95%, or even about 100% of the total reverse enteric coating layer mass, with each possibility representing a separate embodiment.

In certain embodiments, the weight of the coating comprising a reverse enteric polymer is about 0.5% to about 20% of the total orally disintegrating tablet composition mass, including each integer within the specified range. In other embodiments, the weight of the coating comprising a reverse enteric polymer is about 1% to about 15% by weight of the total orally disintegrating tablet composition mass, including each integer within the specified range. In further embodiments, the weight of the coating comprising a reverse enteric polymer is about 5% to about 15% by weight of the total orally disintegrating tablet composition mass, including each integer within the specified range. In yet other embodiments, the weight of the coating comprising a reverse enteric polymer is about 0.5, about 1%, about 2%, about 4%, about 6%, about 8%, about 10%, about 15%, about 20%, or about 25% by weight of the total orally disintegrating tablet composition mass, with each possibility representing a separate embodiment.

In some embodiments, the weight percentage ratio of the plurality of cores (i.e., the active cores, inert seeds coated with an active pharmaceutical ingredient or a combination thereof) to the subcoating layer in the plurality of units is about 0.5:1 to about 4:1, including all iterations of ratios within the specified range. In other embodiments, the weight percentage ratio is about 0.5:1. In yet other embodiments, the weight percentage ratio is about 1:1. In further embodiments, the weight percentage ratio is about 1.8:1. In additional embodiments, the weight percentage ratio is about 2:1.

In some embodiments, the weight percentage ratio of the plurality of cores to the enteric coating layer in the plurality of units is about 0.25:1 to about 3:1, including all iterations of ratios within the specified range. In other embodiments, the weight percentage ratio is about 0.7:1. In yet other embodiments, the weight percentage ratio is about 1:1. In further embodiments, the weight percentage ratio is about 2:1.

In some embodiments, the weight percentage ratio of the plurality of cores to the coating comprising a reverse enteric polymer in the plurality of units is about 0.25:1 to about 8:1, including all iterations of ratios within the specified range. In other embodiments, the weight percentage ratio is about 0.5:1 to about 5:1, including all iterations of ratios within the specified range. In yet other embodiments, the weight percentage ratio is about 1:1. In further embodiments, the weight percentage ratio is about 1.8:1. In certain embodiments, the weight percentage ratio is about 2:1. In further embodiments, the weight percentage ratio is about 2.5:1. In additional embodiments, the weight percentage ratio is about 3:1. In other embodiments, the weight percentage ratio is about 4:1.

In some embodiments, the weight percentage ratio of the coating comprising a reverse enteric polymer to the enteric coating layer in the plurality of units is about 0.25:1 to about 2:1, including all iterations of ratios within the specified range. In other embodiments, the weight percentage ratio is about 0.25:1. In yet other embodiments, the weight percentage ratio is about 0.4:1. In further embodiments, the weight percentage ratio is about 0.8:1. In additional embodiments, the weight percentage ratio is about 1:1. In certain embodiments, the weight percentage ratio is about 1.5:1. In several embodiments, the weight percentage ratio is about 2:1.

In some embodiments, the weight percentage ratio of the subcoating layer to the enteric coating layer in the plurality of units is about 0.25:1 to about 2:1, including all iterations of ratios within the specified range. In other embodiments, the weight percentage ratio is about 0.25:1. In yet other embodiments, the weight percentage ratio is about 0.4:1. In further embodiments, the weight percentage ratio is about 0.7:1. In additional embodiments, the weight percentage ratio is about 1:1. In certain embodiments, the weight percentage ratio is about 1.5:1. In several embodiments, the weight percentage ratio is about 2:1.

In some embodiments, the weight percentage ratio of the coating comprising a reverse enteric polymer to the subcoating layer in the plurality of units is about 0.5:1 to about 3:1, including all iterations of ratios within the specified range. In other embodiments, the weight percentage ratio is about 0.5:1. In yet other embodiments, the weight percentage ratio is about 0.75:1. In further embodiments, the weight percentage ratio is about 1:1. In additional embodiments, the weight percentage ratio is about 1.5:1. In particular embodiments, the weight percentage ratio is about 2:1. In further embodiments, the weight percentage ratio is about 2.5:1.

In some embodiments, the two or more coating layers on the cores substantially cover the cores or the inner layer onto which they are applied. In other embodiments, the two or more coating layers on the cores cover the cores or the inner layer onto which they are applied by at least about 25% of the surface area. In particular embodiment, the two or more coating layers on the cores cover the cores or the adjacent inner layer onto which they are applied by at least about 25%, about 30%, about 35%, about 40%, about 45%, about 50%, about 55%, about 60%, about 65%, about 70%, about 75%, about 80%, about 85%, about 90%, about 95% or about 100% (substantially complete coverage) of the surface area, with each possibility representing a separate embodiment.

Each of the active ingredient coating, subcoating, enteric coating and/or coating comprising reverse enteric polymer layers described herein may additionally include a pharmaceutically acceptable excipient(s), such as, but not limited to, a binder, a filler, a diluent, a surfactant, a glidant, a lubricant, a plasticizer, an anti-tacking agent, an alkaline substance, a tonicity enhancing agent, a wetting agent, a buffering substance, a preservative, a flavoring agent, an opacifier, a colorant, an anti-oxidant or a mixture or combination thereof. Each possibility represents a separate embodiment.

Exemplary and non-limiting binders include povidone (PVP: polyvinyl pyrrolidone), copovidone, hydroxypropyl cellulose (HPC), hydroxypropyl methylcellulose (HPMC), carboxy methyl cellulose (CMC), hydroxyethylcellulose, gelatin, polyethylene oxide, poly ethylene glycol (PEG), poly vinyl alcohol (PVA), acacia, dextrin, magnesium aluminum silicate, starch, and polymethacrylates or a mixture or combination thereof. Each possibility represents a separate embodiment.

Exemplary and non-limiting fillers include lactose, glucose, fructose, sucrose, dicalcium phosphate, sugar alcohols also known as "sugar polyol" such as sorbitol, mannitol, maltitol, lactitol, xylitol, isomalt, erythritol, and hydrogenated starch hydrolysates (a blend of several sugar alcohols), corn starch, potato starch, sodium carboxymethylcellulose, ethylcellulose and cellulose acetate, or a mixture or combination thereof. Each possibility represents a separate embodiment.

Exemplary and non-limiting diluents include dicalcium phosphate dihydrate, sugars, lactose, calcium phosphate, cellulose, kaolin, mannitol, sodium chloride, and dry starch or a mixture or combination thereof. Each possibility represents a separate embodiment.

Exemplary and non-limiting surfactants include non-ionic, zwitterionic, anionic or cationic compounds. Generally, surfactants have a lipophilic and a hydrophilic moiety within the molecule. The surfactant may optionally comprise one or more of soaps, detergents, emulsifiers, and dispersing agents. Suitable surfactants include, but are not limited to, glyceryl monostearate, lanolin alcohols, lecithin, mono- and di-glycerides, monoethanolamine, oleic acid, oleyl alcohol, poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, and emulsifying wax or a mixture or combination thereof. Each possibility represents a separate embodiment.

Exemplary and non-limiting glidant includes silicon dioxide.

Exemplary and non-limiting lubricants include sodium stearyl fumarate, stearic acid, polyethylene glycol or stearates, such as magnesium stearate or a mixture or combination thereof. Each possibility represents a separate embodiment.

Exemplary and non-limiting plasticizers include cetyl alcohol, dibutyl sebacate, polyethylene glycol, polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a mixture or combination thereof. Each possibility represents a separate embodiment.

Exemplary and non-limiting anti-tacking agents include magnesium stearate, calcium stearate, stearic acid, talc, colloidal silicon or a mixture or combination thereof. Each possibility represents a separate embodiment.

Exemplary and non-limiting alkaline substances include organic and inorganic alkaline substances. Suitable organic alkaline substances include, but are not limited to, basic amino acids such as arginine and lysine, amine derivatives and salts, amino sugars such as meglumine, salts of stearic acid such as sodium stearate and the like, with each possibility representing a separate embodiment. Suitable inorganic alkaline agents include, but are not limited to, hydroxides such as sodium or potassium hydroxide, carbonates such as calcium, magnesium or zinc carbonate and the like. Each possibility represents a separate embodiment.

Exemplary and non-limiting tonicity enhancing agents include ionic and non-ionic agents. For example, ionic compounds include, but are not limited to, alkali metal or alkaline earth metal halides, such as, for example, $CaCl_2$ KBr, KCl, LiCl, NaI, NaBr or NaCl, and boric acid or a mixture or combination thereof. Each possibility represents a separate embodiment. Non-ionic tonicity enhancing agents are, for example, urea, glycerol, sorbitol, mannitol, propylene glycol, and dextrose or a mixture or combination thereof. Each possibility represents a separate embodiment.

Exemplary and non-limiting wetting agents include glycerin, starches or a mixture or combination thereof. Each possibility represents a separate embodiment.

Exemplary and non-limiting buffering substances include acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide and magnesium hydroxide or a mixture or combination thereof. Each possibility represents a separate embodiment.

Exemplary and non-limiting preservatives include quaternary ammonium salts such as benzalkonium chloride, benzoxonium chloride or polymeric quaternary ammonium salts; alkyl-mercury salts of thiosalicylic acid, such as, for example, thiomersal, phenylmercuric nitrate, phenylmercuric acetate or phenylmercuric borate; parabens, such as, for example, methylparaben or propylparaben; alcohols, such as, for example, chlorobutanol, benzyl alcohol or phenyl ethanol; guanidine derivatives, such as, for example, chlorohexidine or polyhexamethylene biguanide; sorbic acid and ascorbic acid or a mixture or combination thereof. Each possibility represents a separate embodiment.

Exemplary and non-limiting flavoring agents include, but are not limited to, sweeteners such as sucralose, and synthetic flavor oils and flavoring aromatics, natural oils, extracts from plants, leaves, flowers, and fruits, or a mixture or combinations thereof. Each possibility represents a separate embodiment. Exemplary flavoring agents include cinnamon oils, oil of wintergreen, peppermint oils, clover oil, hay oil, anise oil, *eucalyptus*, vanilla, citrus oil such as lemon oil, orange oil, grape and grapefruit oil, and fruit essences including apple, peach, pear, strawberry, raspberry, cherry, plum, pineapple, and apricot or a mixture or combination thereof. Each possibility represents a separate embodiment.

Exemplary and non-limiting opacifiers include titanium dioxide.

Exemplary and non-limiting colorants include alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide or a mixture or combination thereof. Each possibility represents a separate embodiment.

Exemplary and non-limiting anti-oxidants include tocopherols (e.g., alpha-tocopherol, beta-tocopherol, gamma-tocopherol, or delta-tocopherol), butylated hydroxytoluene (BHT), butylated hydroxyanisole (BHA), citric acid, ascorbic acid, phenolic diterpenes (e.g., carnosic acid, carnosol, rosmanol, epirosmanol, isorosmanol, or methyl carnosate), rosmarinic acid, eugenol, eugenyl acetate, clove bud extract, methanolic extract, tea catechins (e.g., epigallocatechin gallate, epicatechin gallate, epigallocatechin, or epicatechin), or a mixture or combination thereof. Each possibility represents a separate embodiment.

In some embodiments, the plurality of units have a size ranging from about 100 μm to about 1,000 μm, including all integers within the specified range. In other embodiments, the units have a size ranging from about 200 μm to about 900 μm, including all integers within the specified range. In further embodiments, the units have a size ranging from about 300 μm to about 800 μm, including all integers within the specified range. In additional embodiments, the units have a size ranging from about 400 μm to about 700 μm, including all integers within the specified range. In certain embodiments, the units have a size of about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm or about 1,000 μm. Each possibility represents a separate embodiment.

In some embodiments, the plurality of units comprising a plurality of cores having two or more coatings described herein are in an amount of about 20% to about 80% of the total orally disintegrating tablet composition mass, including each integer within the specified range. In other embodiments, the plurality of units are in an amount of about 30% to about 80% of the total orally disintegrating tablet composition mass, including each integer within the specified range. In yet other embodiments, the plurality of units are in an amount of about 40% to about 60% of the total orally disintegrating tablet composition mass, including each integer within the specified range. In further embodiments, the plurality of units are in an amount of about 20%, about 25%, about 30%, about 35%, about 40%, about 45%, or about 50%, about 55%, about 60%, about 65%, about 70%, about 75% or about 80% of the total orally disintegrating tablet composition mass. Each possibility represents a separate embodiment.

In some embodiments, the plurality of units comprises the composition shown in Table 1.

TABLE 1

Exemplary composition of the plurality of units within an orally disintegrating tablet

| Core | | |
|---|---|---|
| Material Class | Exemplary Material(s) | Core Wt % |
| Inert seed | Sugar sphere or microcrystalline cellulose | 15-75 |
| Binder | Hydroxypropylmethylcellulose or polyvinylpyrrolidone | 5-40 |
| Active ingredient | Proton pump inhibitor (omeprazole) | 5-85 |
| Alkaline substance | Sodium stearate | 0.2-10 |
| Total percentage of core | | 100 |
| Total percentage of the cores within an orally disintegrating tablet | | 5-50 |

| Subcoating Layer (optional) | | |
|---|---|---|
| Material Class | Exemplary Material(s) | Subcoating Wt % |
| Binder | Hydroxypropylmethylcellulose or polyvinylpyrrolidone | 20-75 |
| Filler | Mannitol | 15-50 |
| Anti-tacking agent | Talc | 1-12 |
| Total percentage of subcoating layer | | 100 |
| Total percentage of the subcoating layer within an orally disintegrating tablet | | 0-35 |

| Enteric Coating Layer | | |
|---|---|---|
| Material Class | Exemplary Material(s) | Enteric Coating Wt % |
| Acid insoluble polymer | Hydroxypropylmethyl cellulose phthalate or (meth)acrylic acid based copolymer | 50-100 |
| Plasticizer | Triethyl citrate or cetyl alcohol | 5-50 |

TABLE 1-continued

Exemplary composition of the plurality
of units within an orally disintegrating tablet

| | | |
|---|---|---|
| Anti-tacking agent | Talc | 0-15 |
| Opacifier | Titanium dioxide | 0-3 |
| Total percentage of enteric coating layer | | 100 |
| Total percentage of the enteric coating layer within an orally disintegrating tablet | | 10-40 |

Coating Comprising a Reverse Enteric Polymer

| Material Class | Exemplary Material(s) | Coating Comprising a Reverse Enteric Polymer Wt % |
|---|---|---|
| Reverse enteric polymer | Amino methacrylate copolymer (e.g., a methyl methacrylate-butyl methacrylate-dimethylaminoethyl methacrylate copolymer) | 80-100 |
| Glidant | Colloidal silicon dioxide | 0-5 |
| Colorant | Ferric oxide | 0-3 |
| Total percentage of coating comprising a reverse enteric polymer layer | | 100 |
| Total percentage of the coating comprising a reverse enteric polymer within an orally disintegrating tablet | | 0.5-20 |

In addition to the plurality of units, the orally disintegrating tablet according to the principles described herein comprises a disintegrant and optionally one or more pharmaceutically acceptable excipients. In some embodiments, the additional excipients comprise one or more or all of the pharmaceutically acceptable excipients selected from a binder, a filler, a diluent, a surfactant, a glidant, a lubricant, a plasticizer, an anti-tacking agent, an alkaline substance, a tonicity enhancing agent, a wetting agent, a buffering substance, a preservative, a flavoring agent, an opacifier, a colorant, an anti-oxidant or a mixture or combination thereof. Each possibility represents a separate embodiment. The one or more optional pharmaceutically acceptable excipients suitable for being incorporated into the orally disintegrating tablet as tablet excipients in addition to the disintegrant, include all of the aforementioned excipients described herein to be optionally added to the various coating layers. It is to be understood that the aforementioned list is not meant to be exclusive, but instead merely representative of the classes of excipients and the particular excipients that may be used in the tablets described herein (see also, Rowe, R. C.; Sheskey, P. J.; Owen Sian C. *Handbook Of Pharmaceutical Excipients*; Pharmaceutical Press: London, 2006).

In some embodiments, the pharmaceutically acceptable tablet excipients (including the disintegrant) are in an amount of not more than about 70% by weight of the orally disintegrating tablet. In other embodiments, these tablet excipients are in an amount of not more than about 60% by weight of the orally disintegrating tablet. Exemplary excipients that may be comprised in the orally disintegrating tablets as tablet excipients and their typical weight percentages are shown in Table 2.

TABLE 2

Exemplary Tablet Excipients

| Excipient Class | Exemplary Excipient(s) | Matrix Wt % |
|---|---|---|
| Disintegrant | Crospovidone | 5-50 |
| Filler | Microcrystalline Cellulose | 5-30 |
| Binder | Polyvinyl pyrrolidone; Hydroxy propyl methyl cellulose | 0-65 |
| Flavoring agent | Sucralose; Strawberry flavorant | 0-7 |
| Antioxidant | Ascorbic acid | 0-5 |
| Glidant | Colloidal silicon dioxide | 0-5 |
| Lubricant | Sodium stearyl fumarate | 0-15 |
| Anti-tacking agent | Talc | 0-15 |
| Colorant | Ferric oxide; Aluminum powder | 0-5 |
| Total percentage of the matrix excipients | | 100 |
| Total Percentage within an Orally Disintegrating Tablet | | 0-70 |

Exemplary and non-limiting disintegrants include cross-linked polyvinyl pyrrolidone (crospovidone), sodium starch glycolate, cross-linked sodium carboxymethyl cellulose (e.g., croscarmellose sodium), cross-linked derivatives of starch, pregelatinized starch (starch 1500), microcrystalline starch, water insoluble starch, a cellulose derivative, sodium carboxymethyl cellulose, calcium carboxymethyl cellulose, low substituted hydroxypropyl cellulose, or a mixture or combination thereof. Each possibility represents a separate embodiment.

Additional and non-limiting disintegrants include silicates, carbonates, polyoxyethylene sorbitan fatty acid esters, stearic monoglyceride, guar gum, magnesium aluminum silicate, a sugar alcohol, and lactose or a mixture or combination thereof. Each possibility represents a separate embodiment.

Exemplary and non-limiting sugar alcohols include mannitol, sorbitol, maltitol, xylitol, arabitol, isomalt, erythritol, glycerol, and lactitol, or a mixture or combination thereof. Each possibility represents a separate embodiment.

Exemplary and non-limiting cellulose derivatives include methylcellulose and microcrystalline cellulose or a mixture or combination thereof. Each possibility represents a separate embodiment.

In some embodiments, the one or more disintegrants are in an amount of about 2% to about 50% of the total weight of the orally disintegrating tablet composition mass, including each integer within the specified range. In other embodiments, the one or more disintegrants are in an amount of about 2% to about 40% of the total weight of the orally disintegrating tablet composition mass, including each integer within the specified range. In yet other embodiments, the one or more disintegrants are in an amount of about 2% to about 30% of the total weight of the orally disintegrating tablet composition mass, including each integer within the specified range. In further embodiments, the one or more disintegrants are in an amount of about 2% to about 25% of the total weight of the orally disintegrating tablet composition mass, including each integer within the specified range. In additional embodiments, the one or more disintegrants are in an amount of about 2%, about 4%, about 6%, about 8%, about 10%, about 15%, about 20%, about 25%, about 30%, about 35%, about 40%, about 45%, or about 50% of the total weight of the orally disintegrating tablet composition mass. Each possibility represents a separate embodiment.

In some embodiments, the weight percentage ratio of the plurality of units to the disintegrant and one or more optional excipients forming the tablet matrix is about 0.25:1 to about 4:1, including all iterations of ratios within the specified range. In other embodiments, the weight percentage ratio is about 0.5:1. In yet other embodiments, the weight percentage ratio is about 0.75:1. In further embodiments, the weight percentage ratio is about 1:1. In additional embodiments, the weight percentage ratio is about 1.5:1. In certain embodiments, the weight percentage ratio is about 2:1. In further embodiments, the weight percentage ratio is about 3:1. In yet other embodiments, the weight percentage ratio is about 4:1.

Methods of Manufacturing Orally Disintegrating Tablets

Some embodiments described herein include a method for preparing orally disintegrating tablets. In some embodiments, the method comprises preparing one or more of an active ingredient layer solution or dispersion, a subcoating solution or dispersion, an enteric coating solution or dispersion, and a solution or dispersion coating layer comprising a reverse enteric polymer. In various embodiments, suitable solvents are used to dissolve or suspend one or more of the coating mixture ingredients. Such solvents include, but are not limited to, water, protic or aprotic organic solvents. Exemplary and non-limiting protic or aprotic organic solvents include isopropyl alcohol, ethanol, and acetone or a mixture or combinations thereof, with each possibility representing a separate embodiment.

In some embodiments, the active ingredient coating layer mixture is prepared by mixing one or more active ingredients (e.g., a proton pump inhibitor), a solvent (e.g., water) and optionally one or more of a binder (e.g., HPMC) and an alkaline agent (e.g., sodium stearate) to form an active ingredient layer dispersion or solution. The optional subcoating solution or dispersion is prepared by mixing one or more of a binder (e.g., HPMC), a filler (e.g., mannitol), and an anti-tacking agent (e.g., talc), in a solvent (e.g., water). The enteric coating solution or dispersion is prepared by mixing one or more of an acid-insoluble enteric polymer (e.g., HPMCP), one or more plasticizers (e.g., triethyl citrate and cetyl alcohol), in a solvent (e.g., ethanol and acetone), and optionally one or more anti-tacking agent (e.g., talc), and one or more opacifiers (e.g., titanium dioxide). The coating layer comprising a reverse enteric polymer is prepared by mixing one or more reverse enteric polymers (e.g., a methyl methacrylate-butyl methacrylate-dimethylaminoethyl methacrylate copolymer) in a solvent (e.g., alcohol and water) and optionally one or more glidants (e.g., colloidal silicon dioxide), and one or more colorants (e.g., ferric oxide).

Alternatively, in some embodiments, the core is an active core and does not require an active ingredient coating layer, but rather may be prepared, for example, by first preparing a mixture of one or more of a binder, filler, and alkaline agent with one or more active ingredients and generating a core (e.g., using granulation, extrusion, or spheronization techniques as is known in the art).

In some embodiments, the method of manufacturing an orally disintegrating tablet comprises: (a) generating a plurality of cores comprising a therapeutically effective amount of a proton pump inhibitor; (b) applying a solution or dispersion comprising an enteric polymer to the plurality of cores of step (a) thereby obtaining a plurality of enteric coated cores; (c) applying a solution or dispersion comprising a reverse enteric polymer to the enteric coated cores of step (b) thereby obtaining a plurality of units; (d) mixing the plurality of units with at least one tablet excipient comprising a disintegrant thereby obtaining a blend; and (e) compressing the blend of step (d) thereby obtaining the compressed orally disintegrating tablet. In some embodiments, the step of generating the plurality of cores comprises applying a solution or dispersion comprising a therapeutically effective amount of a proton pump inhibitor to a plurality of inert seeds. In other embodiments, the method for manufacturing an orally disintegrating tablet comprises an additional step prior to step (b) of applying the enteric coating, the additional step (a1) comprising: applying a subcoating solution or dispersion comprising at least one of hydroxypropyl methylcellulose, hydroxypropyl cellulose, polyvinylpyrrolidone, polyethylene glycol, polyvinyl alcohol or a mixture or combination thereof to the plurality of cores of step (a) thereby obtaining a subcoating between the cores and the enteric coating.

In some embodiments, the methods of manufacturing further comprise the steps of sieving the coated cores between each coating step. It is believed that the sieving steps eliminate oversized agglomerates. In some embodiments, the solvent(s) is vaporized or evaporated from each of the respective coating layers.

The different coating layers can be applied to the cores to generate the plurality of units described herein by conventional coating techniques known in the art, see, Remington, J. P.; Beringer, P. Remington: *The Science and Practice of Pharmacy*; Lippincott Williams & Wilkins: Philadelphia, 2006. For example, fluidized coating methods including, but not limited to, pan coating, Wurster fluidized bed coating, fluidized bed bottom sprayed coating or a turbo jet-technology can be used. A fluidized bed is a bed of solid particles which are suspended in a stream of air or gas passing upward through the particles, in which the coating material is aerosolized. As the air travels through the particle bed, the particles are mixed in the stream of gas or air with the coating material, thereby being coated and also dried.

Alternatively, a dry powder layering may be used to apply the coating layers. Dry powder coating processes may be performed using many known systems, such as, for example, CF-Granulator (Freund Industrial, Tokyo, Japan), Granurex (Vector Corporation, Marion, Iowa, USA), GS HP/25 equipment (GS Coating System, Italy), Centrifugal Fluid Bed Granulator (Glatt, Germany) and other appropriate systems known in the art.

At the end of the coating process, the coated cores may be dried for an additional period of time to allow any residual solvent to evaporate. The rate, amount, homogeneity, inter- and intra-uniformity, efficiency, quality, and yield of the coating may be controlled by parameters such as batch size, rotor speed, binder spray rate, powder addition rate, inlet and outlet air temperature, bed temperature, atomization air pressure, air flap and air flow as is known in the art.

The steps of mixing or blending the plurality of units with at least one pharmaceutically acceptable excipient (e.g., a disintegrant and optionally additional excipients) prior to compression can be performed using any pharmaceutical blending process known in the art. For example, the mixing or blending process can be achieved using any suitable type of mixer or blender. Non-limiting examples include: simple paddle mixer, ribbon and/or tumbling mixers, plow blenders and drum agglomerators, V-blenders, double cone blenders, slant cone blenders, twin shell blenders, e.g., Patterson Kelley V Blenders, Gemco double cone blenders, diffusion blenders and the like.

The compression process may be achieved using any suitable tableting equipment. Non-limiting examples include: mini press, single or double punch or rotary tablet press such as Killian, Korsch, Colton, Manesty, Stokes, Vector and the like, among others.

Methods of Increasing the Compressibility of Orally Disintegrating Tablets

The orally disintegrating tablets described herein are resilient to breakage. The coating layer on the plurality of units which comprises a reverse enteric polymer as described herein decreases tablet friability and increases tablet hardness. The hardness of a tablet refers to the force used to break or fracture the tablet. For example, a fracture test or bending test may be used to determine the force at which the tablet fractures or bends. Commercially available testers include, but are not limited to, the CT3 Analyzer from Brookfield Engineering. Friability tests the resilience of the tablets to fracturing or breaking following repetitive dropping. These tests are usually performed using a rotating wheel having a baffle followed by assessing tablet breakage. Commercial analyzers include, but are not limited to, those from the Pharma Test Group, such as the PTF 20 E or PTF 20ER. The techniques for measuring tablet hardness and friability are well known in the pharmaceutical formulary sciences, see, for example the United States Pharmacopeia (USP #39 NF34, particularly Tablet Breaking Force <1217> and Tablet Friability <1216>).

In some embodiments, the orally disintegrating tablets have a friability of less than about 5% when about 10 kN to about 50 kN of compression force is applied during manufacturing. In other embodiments, the orally disintegrating tablets have a friability of less than about 3% when about 10 kN to about 50 kN of compression force is applied during manufacturing. In yet other embodiments, the orally disintegrating tablets have a friability of less than about 1% when about 10 kN to about 50 kN of compression force is applied during manufacturing. In further embodiments, the orally disintegrating tablets have a friability of less than about 0.75% when about 10 kN to about 50 kN of compression force is applied during manufacturing. In additional embodiments, the orally disintegrating tablets have a friability of less than about 0.5% when about 10 kN to about 50 kN of compression force is applied during manufacturing. In particular embodiments, the orally disintegrating tablets have a friability of less than about 0.3% when about 10 kN to about 50 kN of compression force is applied during manufacturing. In yet other embodiments, the orally disintegrating tablets have a friability of less than about 0.1% when about 10 kN to about 50 kN of compression force is applied during manufacturing.

In some embodiments, the orally disintegrating tablets have a hardness of about 20 N to about 100 N when about 10 kN to about 50 kN of compression force is applied during manufacturing, including all iterations of integers within the specified range. In other embodiments, the orally disintegrating tablets have a hardness of about 20 N to about 80 N when about 10 kN to about 50 kN of compression force is applied during manufacturing, including all iterations of integers within the specified range. In yet other embodiments, the orally disintegrating tablets have a hardness of about 30 N to about 70 N when about 10 kN to about 50 kN of compression force is applied during manufacturing, including all iterations of integers within the specified range. In further embodiments, the orally disintegrating tablets have a hardness of about 30 N to about 50 N when about 10 kN to about 50 kN of compression force is applied during manufacturing, including all iterations of integers within the specified range. In additional embodiments, the orally disintegrating tablets have a hardness of about 20 N, about 25 N, about 30 N, about 35 N, about 40 N, about 45 N, about 50 N, about 60 N, about 65 N, about 70 N, about 75 N, about 80 N, about 85 N, about 90 N, about 95 N, or about 100 N, when about 10 kN to about 50 kN of compression force is applied during manufacturing. Each possibility represents a separate embodiment.

Some embodiments described herein are methods for increasing the compressibility of an orally disintegrating tablet. Compressibility is measured as a function of hardness or friability. According to the principles described herein, the orally disintegration tablets have increased hardness and/or reduced friability compared to reference tablets that do not have a coating layer comprising a reverse enteric polymer that are made by the same manufacturing processes. Accordingly, the orally disintegrating tablets disclosed herein are more compressible (i.e. characterized by improved compressibility). In some embodiments, the method of increasing compressibility comprises coating at least a portion of the enteric coated cores with a coating layer comprising a reverse enteric polymer. In other embodiments, the reverse enteric polymer comprises a methyl methacrylate-butyl methacrylate-dimethylaminoethyl methacrylate copolymer.

Thus, in some embodiments, there is provided a method for increasing the compressibility of a compressed orally disintegrating tablet comprising a disintegrant and a plurality of units comprising enteric coated cores, the method comprises applying a coating comprising a reverse enteric polymer over the enteric coated cores, wherein the increased compressibility comprises one or more of a decreased friability or an increased hardness compared to a compressed orally disintegrating tablet not comprising a coating comprising a reverse enteric polymer when a substantially identical compression force is applied during manufacturing of the tablet.

As used herein, "substantially identical compression force" refers to a compression force used to generate a tablet (e.g., an orally disintegrating tablet according to the disclosure) that varies in less than about 20%, for example, about 15%, about 10%, about 5% or is substantially identical to a compression force used to generate a reference tablet.

In some embodiments, the compression force used during manufacturing is from about 10 kN to about 100 kN, including each integer within the specified range. In other embodiments, the compression force is from about 10 kN to about 50 kN, including each integer within the specified range. In yet other embodiments, the compression force is about 10 kN, about 20 kN, about 30 kN, about 40 kN, about 50 kN, about 60 kN, about 70 kN, about 80 kN, about 90 kN, or about 100 kN, with each possibility representing a separate embodiment.

In some embodiments, the measured decreased friability by using the methods of increasing compressibility is about 0.75% or less when about 10 kN to about 100 kN of compression force is applied during manufacturing of the tablet. In other embodiments, the decreased friability is about 0.75% or less when about 10 kN to about 50 kN of compression force is applied during manufacturing of the tablet. In yet other embodiments, the decreased friability is about 0.5% or less when about 10 kN to about 50 kN of compression force is applied during manufacturing of the tablet. In further embodiments, the decreased friability is about 0.3% or less when about 10 kN to about 50 kN of compression force is applied during manufacturing of the tablet. In yet other embodiments, the decreased friability is about 0.1% or less when about 10 kN to about 50 kN of compression force is applied during manufacturing of the tablet.

In some embodiments, the measured increased hardness of the orally disintegrating tablets is about 20 N to about 100 N when about 10 kN to about 100 kN of compression force is applied during manufacturing of the tablet. In other embodiments, the increased hardness is about 20 N to about 100 N when about 10 kN to about 50 kN of compression force is applied during manufacturing of the tablet.

Methods of Using Orally Disintegrating Tablets

In some embodiments, the orally disintegrating tablets described herein provide a dosage form of an active pharmaceutical ingredient for administration to a subject in need thereof. In one embodiment, the subject in need thereof is a mammal in need of treatment. In another embodiment, the subject is a human in need of treatment. In certain embodiments, the orally disintegrating tablet disclosed herein is useful for inhibiting gastric acid secretion. In some embodiments, the orally disintegrating tablet disclosed herein is useful for the treatment or prophylaxis of a gastric disorder. In one embodiment, the gastric disorder comprises gastric reflux (e.g., GERD or GORD), laryngopharyngeal reflux, laryngitis, dyspepsia, Barrett's esophagus, eosinophilic esophagitis, gastritis, gastrinomas (e.g., Zollinger-Ellison syndrome), peptic ulcer, or excessive *Helicobacter pylori*. Each possibility represents a separate embodiment.

The term "treating" as used herein refers to stopping or slowing down the progression of the disease. The term "treating" further includes the reduction in the occurrence of various symptoms associated with gastric acid secretion.

The amount of a composition to be administered depends on various factors including, but not limited to, the subject being treated (age and gender) and the severity of the disease, and can be determined by the judgment of the prescribing physician. Because of patient-to-patient variability, dosages are a guideline only and the physician may adjust doses of the compounds to achieve the level of effective treatment that the physician considers appropriate for the patient. In considering the degree of treatment desired, the physician must balance a variety of factors such as the age of the patient and the presence of other diseases or conditions.

The dosage form can be administered, for example, 1×, 2×, 3×, 4×, 5×, 6×, or even more times per day. One or more dosage form can be administered, for example, for 1, 2, 3, 4, 5, 6, 7, 8, 9, 10, 11, 12, 13 or 14 days, or even longer. One or more dosage forms can be administered, for example, for 1, 2, 3, 4 weeks, or even longer. One or more dosage forms can be administered at a regular interval until the subject does not require treatment, prophylaxis, or amelioration of the aforementioned gastric disorders and symptoms associated therewith.

Some embodiments described herein provide a kit for dispensing the orally disintegrating tablet compositions comprising: (a) at least one orally disintegrating tablet described herein comprising an active pharmaceutical ingredient (e.g., a proton pump inhibitor); (b) at least one receptacle comprising a moisture proof packaging comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; and (c) optionally, an insert comprising instructions or prescribing information for the active pharmaceutical ingredient described herein.

Some embodiments described herein, are orally disintegrating tablets according to any of the formulations shown in the Tables or Examples described herein. Any of the components of the formulations shown in the Tables or Examples can be increased, decreased, combined, recombined, switched, or removed to provide for a formulation comprising about 100% by weight.

As used herein and in the appended claims, the term "about" refers to ±10%.

As used herein and in the appended claims, the singular forms "a", "an", and "the" include plural references unless the context clearly dictates otherwise. Thus, for example, reference to "a layer" includes a plurality of such layers and equivalents thereof known to those skilled in the art, and so forth. It should be noted that the term "and" or the term "or" are generally employed in its sense including "and/or" unless the context clearly dictates otherwise.

It will be apparent to one of ordinary skill in the relevant art that suitable modifications and adaptations to the compositions, formulations, methods, processes, kits and applications described herein can be made without departing from the scope of any embodiments or aspects thereof. The compositions, kits and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Furthermore, the foregoing discussion discloses and describes merely exemplary embodiments.

EXAMPLES

Example 1

Orally disintegrating tablets were prepared as follows: inert sugar spheres were coated with a drug layer containing 20 mg omeprazole, a binder (hydroxypropylmethyl cellulose; HPMC) and an alkaline substance (sodium stearate). A subcoating layer containing HPMC, mannitol and talc and an enteric coating layer containing hydroxypropylmethyl cellulose phthalate as the enteric polymer and cetyl alcohol and triethyl citrate as plasticizers were then sequentially applied. An over-coating layer containing amino methacrylate copolymer as the reverse enteric polymer was then applied. The coated units were blended with a mixture of powders containing crospovidone as disintegrant, lubricated (e.g. with sodium stearyl fumarate) and compressed into orally disintegrating tablets in a tablet press. Exemplary orally disintegrating tablets according to the disclosure are shown in Tables 3-13. The tablet thickness, friability, disintegration, and hardness results of these exemplary orally disintegrating tablets as well as the compression and ejection forces applied are shown in Table 14.

TABLE 3

Exemplary Orally Disintegrating Tablet

| Layer and Materials | Formulation 1 | |
|---|---|---|
| | Mg/tab | Wt %/coating |
| Core | | |
| Seed (Sugar spheres) | 18.2 | 37.7 |
| Omeprazole | 20.0 | 41.4 |
| HPMC | 10.0 | 20.7 |
| Sodium Stearate | 0.1 | 0.2 |
| Total | 48.3 | 100 |
| Subcoating Layer | | |
| HPMC | 15.1 | 56.6 |
| Mannitol | 10.1 | 37.8 |
| Talc | 1.5 | 5.6 |
| Total | 26.7 | 100 |
| Enteric Coating Layer | | |
| HPMC phthalate | 46.7 | 72.4 |
| Cetyl alcohol | 8.4 | 13.0 |
| Triethyl citrate | 3.8 | 5.9 |
| Talc | 4.6 | 7.1 |
| Titanium dioxide | 1.0 | 1.6 |
| Total | 64.5 | 100 |
| Coating with a Reverse Enteric Polymer | | |
| Amino methacrylate copolymer (a methyl methacrylate-butyl methacrylate-dimethylaminoethyl methacrylate copolymer) | 12.8 | 48.7 |
| Triethyl citrate | 1.3 | 4.9 |
| Talc | 12.2 | 46.4 |
| Total | 26.3 | 100 |
| Additional Tableting Excipients | | |
| | Mg/tab | Wt %/tab |
| Pharmaburst ® | 205.5 | 48.9 |
| Crospovidone | 25.0 | 6.0 |
| Sucralose | 6.0 | 1.4 |
| Ascorbic acid | 4.1 | 1.0 |
| Mint flavor | 3.1 | 0.7 |
| Colloidal silicon dioxide | 2.1 | 0.5 |
| Sodium stearyl fumarate | 8.4 | 2.0 |
| Total | 254.2 | 60.5 |
| Total Tablet Weight | 420 mg | |

TABLE 4

Exemplary Orally Disintegrating Tablet

| Layer and Materials | Formulation 2 | |
|---|---|---|
| | Mg/tab | Wt %/coating |
| Core | | |
| Seed (Sugar spheres) | 18.2 | 37.7 |
| Omeprazole | 20.0 | 41.4 |
| HPMC | 10.0 | 20.7 |
| Sodium Stearate | 0.1 | 0.2 |
| Total | 48.3 | 100 |
| Subcoating Layer | | |
| HPMC | 15.1 | 56.6 |
| Mannitol | 10.1 | 37.8 |
| Talc | 1.5 | 5.6 |
| Total | 26.7 | 100 |
| Enteric Coating Layer | | |
| HPMC phthalate | 46.7 | 72.4 |
| Cetyl alcohol | 8.4 | 13.0 |
| Triethyl citrate | 3.8 | 5.9 |
| Talc | 4.6 | 7.1 |
| Titanium dioxide | 1.0 | 1.6 |
| Total | 64.5 | 100 |
| Coating with a Reverse Enteric Polymer | | |
| Amino methacrylate copolymer (a methyl methacrylate-butyl methacrylate-dimethylaminoethyl methacrylate copolymer) | 25.6 | 48.7 |
| Triethyl citrate | 2.6 | 4.9 |
| Talc | 24.4 | 46.4 |
| Total | 52.6 | 100 |
| Additional Tableting Excipients | | |
| | Mg/tab | Wt %/tab |
| Pharmaburst ® | 179.2 | 42.6 |
| Crospovidone | 25.0 | 6.0 |
| Sucralose | 6.0 | 1.4 |
| Ascorbic acid | 4.1 | 1.0 |
| Mint flavor | 3.1 | 0.7 |
| Colloidal silicon dioxide | 2.1 | 0.5 |
| Sodium stearyl fumarate | 8.4 | 2.0 |
| Total | 227.9 | 54.3 |
| Total Tablet Weight | 420 mg | |

TABLE 5

Exemplary Orally Disintegrating Tablet

| Layer and Materials | Formulation 3 | |
|---|---|---|
| | Mg/tab | Wt %/coating |
| Core | | |
| Seed (Sugar spheres) | 18.2 | 37.7 |
| Omeprazole | 20.0 | 41.4 |

TABLE 5-continued

| | | |
|---|---|---|
| HPMC | 10.0 | 20.7 |
| Sodium Stearate | 0.1 | 0.2 |
| Total | 48.3 | 100 |
| Subcoating Layer | | |
| HPMC | 15.1 | 56.6 |
| Mannitol | 10.1 | 37.8 |
| Talc | 1.5 | 5.6 |
| Total | 26.7 | 100 |
| Enteric Coating Layer | | |
| HPMC phthalate | 46.7 | 72.4 |
| Cetyl alcohol | 8.4 | 13.0 |
| Triethyl citrate | 3.8 | 5.9 |
| Talc | 4.6 | 7.1 |
| Titanium dioxide | 1.0 | 1.6 |
| Total | 64.5 | 100 |
| Coating with a Reverse Enteric Polymer | | |
| Amino methacrylate copolymer (a methyl methacrylate-butyl methacrylate-dimethylaminoethyl methacrylate copolymer) | 25.6 | 47.7 |
| Triethyl citrate | 2.6 | 4.8 |
| Talc | 24.4 | 45.4 |
| Colloidal silicon dioxide | 0.9 | 1.7 |
| Sucralose | 0.2 | 0.4 |
| Total | 53.7 | 100 |
| Additional Tableting Excipients | | |
| | Mg/tab | Wt %/tab |
| Pharmaburst ® | 179.9 | 42.8 |
| Crospovidone | 25.0 | 6.0 |
| Sucralose | 5.3 | 1.3 |
| Ascorbic acid | 4.1 | 1.0 |
| Mint flavor | 2.0 | 0.5 |
| Colloidal silicon dioxide | 2.1 | 0.5 |
| Sodium stearyl fumarate | 8.4 | 2.0 |
| Total | 226.8 | 54.0 |
| Total Tablet Weight | | 420 mg |

TABLE 6

Exemplary Orally Disintegrating Tablet

| | Formulation 4 | |
|---|---|---|
| Layer and Materials | Mg/tab | Wt %/coating |
| Core | | |
| Seed (Sugar spheres) | 17.7 | 36.8 |
| Omeprazole | 20.0 | 41.5 |
| HPMC | 10.0 | 20.8 |
| Sodium Stearate | 0.45 | 0.9 |
| Total | 48.15 | 100 |
| Subcoating Layer | | |
| HPMC | 15.0 | 55.9 |
| Mannitol | 10.0 | 37.2 |
| Talc | 1.85 | 6.9 |
| Total | 26.85 | 100 |
| Enteric Coating Layer | | |
| HPMC phthalate | 47.0 | 72.3 |
| Cetyl alcohol | 8.5 | 13.1 |
| Triethyl citrate | 4.0 | 6.2 |
| Talc | 4.5 | 6.9 |
| Titanium dioxide | 1.0 | 1.5 |
| Total | 65 | 100 |
| Coating with a Reverse Enteric Polymer | | |
| Amino methacrylate copolymer (a methyl methacrylate-butyl methacrylate-dimethylaminoethyl methacrylate copolymer) | 26.0 | 95.4 |
| Colloidal silicon dioxide | 1.0 | 3.7 |
| Ferric oxide | 0.25 | 0.9 |
| Total | 27.25 | 100 |
| Additional Tableting Excipients | | |
| | Mg/tab | Wt %/tab |
| Pharmaburst ® | 132.4 | 39.4 |
| Crospovidone | 19.2 | 5.7 |
| Sucralose | 4.0 | 1.2 |
| Ascorbic acid | 3.0 | 0.9 |
| Strawberry flavor | 1.2 | 0.4 |
| Colloidal silicon dioxide | 1.6 | 0.5 |
| Sodium stearyl fumarate | 6.7 | 2.0 |
| Red oxide | 0.65 | 0.2 |
| Total | 168.75 | 50.2 |
| Total Tablet Weight | | 336 mg |

TABLE 7

Exemplary Orally Disintegrating Tablet

| | Formulation 5 | |
|---|---|---|
| Layer and Materials | Mg/tab | Wt %/coating |
| Core | | |
| Seed (Sugar spheres) | 17.7 | 36.8 |
| Omeprazole | 20.0 | 41.5 |
| HPMC | 10.0 | 20.8 |
| Sodium Stearate | 0.45 | 0.9 |
| Total | 48.15 | 100 |
| Subcoating Layer | | |
| HPMC | 15.0 | 55.9 |
| Mannitol | 10.0 | 37.2 |
| Talc | 1.85 | 6.9 |
| Total | 26.85 | 100 |
| Enteric Coating Layer | | |
| HPMC phthalate | 47.0 | 72.3 |
| Cetyl alcohol | 8.5 | 13.1 |
| Triethyl citrate | 4.0 | 6.2 |

TABLE 7-continued

| | | |
|---|---|---|
| Talc | 4.5 | 6.9 |
| Titanium dioxide | 1.0 | 1.5 |
| Total | 65 | 100 |

Coating with a Reverse Enteric Polymer

| | | |
|---|---|---|
| Amino methacrylate copolymer (a methyl methacrylate-butyl methacrylate-dimethylaminoethyl methacrylate copolymer) | 26.0 | 95.4 |
| Colloidal silicon dioxide | 1.0 | 3.7 |
| Ferric oxide | 0.25 | 0.9 |
| Total | 27.25 | 100 |

Additional Tableting Excipients

| | Mg/tab | Wt %/tab |
|---|---|---|
| Pharmaburst ® | 202.0 | 48.1 |
| Crospovidone | 28.0 | 6.7 |
| Sucralose | 5.5 | 1.3 |
| Ascorbic acid | 4.5 | 1.1 |
| Strawberry flavor | 1.2 | 0.3 |
| Colloidal silicon dioxide | 2.4 | 0.6 |
| Sodium stearyl fumarate | 8.4 | 2.0 |
| Red oxide | 0.75 | 0.2 |
| Total | 252.75 | 60.2 |
| Total Tablet Weight | 420 mg | |

TABLE 8

Exemplary Orally Disintegrating Tablet

| | Formulation 6 | |
|---|---|---|
| Layer and Materials | Mg/tab | Wt %/coating |

Core

| | | |
|---|---|---|
| Seed (Sugar spheres) | 17.7 | 36.8 |
| Omeprazole | 20.0 | 41.5 |
| HPMC | 10.0 | 20.8 |
| Sodium Stearate | 0.45 | 0.9 |
| Total | 48.15 | 100 |

Subcoating Layer

| | | |
|---|---|---|
| HPMC | 15.0 | 55.9 |
| Mannitol | 10.0 | 37.2 |
| Talc | 1.85 | 6.9 |
| Total | 26.85 | 100 |

Enteric Coating Layer

| | | |
|---|---|---|
| HPMC phthalate | 47.0 | 72.3 |
| Cetyl alcohol | 8.5 | 13.1 |
| Triethyl citrate | 4.0 | 6.2 |
| Talc | 4.5 | 6.9 |
| Titanium dioxide | 1.0 | 1.5 |
| Total | 65 | 100 |

Coating with a Reverse Enteric Polymer

| | | |
|---|---|---|
| Amino methacrylate copolymer (a methyl methacrylate-butyl methacrylate-dimethylaminoethyl methacrylate copolymer) | 26.0 | 96.3 |
| Colloidal silicon dioxide | 0.75 | 2.8 |
| Ferric oxide | 0.25 | 0.9 |
| Total | 27 | 100 |

Additional Tableting Excipients

| | Mg/tab | Wt %/tab |
|---|---|---|
| Pharmaburst ® | 108.9 | 32.4 |
| Microcrystalline cellulose (MCC) | 26.3 | 7.8 |
| Crospovidone | 19.2 | 5.7 |
| Sucralose | 4.0 | 1.2 |
| Ascorbic acid | 3.0 | 0.9 |
| Strawberry flavor | 1.2 | 0.4 |
| Colloidal silicon dioxide | 1.6 | 0.5 |
| Sodium stearyl fumarate | 4.2 | 1.3 |
| Red oxide | 0.6 | 0.2 |
| Total | 169 | 50.3 |
| Total Tablet Weight | 336 mg | |

TABLE 9

Exemplary Orally Disintegrating Tablet

| | Formulation 7 | |
|---|---|---|
| Layer and Materials | Mg/tab | Wt %/coating |

Core

| | | |
|---|---|---|
| Seed (Sugar spheres) | 17.7 | 36.8 |
| Omeprazole | 20.0 | 41.5 |
| HPMC | 10.0 | 20.8 |
| Sodium Stearate | 0.45 | 0.9 |
| Total | 48.15 | 100 |

Subcoating Layer

| | | |
|---|---|---|
| HPMC | 15.0 | 55.9 |
| Mannitol | 10.0 | 37.2 |
| Talc | 1.85 | 6.9 |
| Total | 26.85 | 100 |

Enteric Coating Layer

| | | |
|---|---|---|
| HPMC phthalate | 47.0 | 72.3 |
| Cetyl alcohol | 8.5 | 13.1 |
| Triethyl citrate | 4.0 | 6.2 |
| Talc | 4.5 | 6.9 |
| Titanium dioxide | 1.0 | 1.5 |
| Total | 65 | 100 |

Coating with a Reverse Enteric Polymer

| | | |
|---|---|---|
| Amino methacrylate copolymer (a methyl methacrylate-butyl methacrylate-dimethylaminoethyl methacrylate copolymer) | 26.0 | 96.3 |
| Colloidal silicon dioxide | 0.75 | 2.8 |
| Ferric oxide | 0.25 | 0.9 |
| Total | 27 | 100 |

Additional Tableting Excipients

| | Mg/tab | Wt %/tab |
|---|---|---|
| Pharmaburst ® | 98.7 | 29.4 |
| Microcrystalline cellulose (MCC) | 26.3 | 7.8 |

TABLE 9-continued

| | | |
|---|---|---|
| Crospovidone | 26.9 | 8.0 |
| Sucralose | 4.0 | 1.2 |
| Ascorbic acid | 3.0 | 0.9 |
| Strawberry flavor | 1.2 | 0.4 |
| Colloidal silicon dioxide | 1.6 | 0.5 |
| Sodium stearyl fumarate | 6.7 | 2.0 |
| Red oxide | 0.6 | 0.2 |
| | | |
| Total | 169 | 50.3 |
| Total Tablet Weight | 336 mg | |

TABLE 10

Exemplary Orally Disintegrating Tablet

| | Formulation 8 | |
|---|---|---|
| Layer and Materials | Mg/tab | Wt %/coating |
| Core | | |
| Seed (Sugar spheres) | 17.7 | 36.8 |
| Omeprazole | 20.0 | 41.5 |
| HPMC | 10.0 | 20.8 |
| Sodium Stearate | 0.45 | 0.9 |
| Total | 48.15 | 100 |
| Subcoating Layer | | |
| HPMC | 15.0 | 55.9 |
| Mannitol | 10.0 | 37.2 |
| Talc | 1.85 | 6.9 |
| Total | 26.85 | 100 |
| Enteric Coating Layer | | |
| HPMC phthalate | 47.0 | 72.3 |
| Cetyl alcohol | 8.5 | 13.1 |
| Triethyl citrate | 4.0 | 6.2 |
| Talc | 4.5 | 6.9 |
| Titanium dioxide | 1.0 | 1.5 |
| Total | 65 | 100 |
| Coating with a Reverse Enteric Polymer | | |
| Amino methacrylate copolymer (a methyl methacrylate-butyl methacrylate-dimethylaminoethyl methacrylate copolymer) | 26.0 | 96.3 |
| Colloidal silicon dioxide | 0.75 | 2.8 |
| Ferric oxide | 0.25 | 0.9 |
| Total | 27 | 100 |
| Additional Tableting Excipients | | |
| | Mg/tab | Wt %/tab |
| Pharmaburst ® | 123.9 | 36.9 |
| Microcrystalline cellulose (MCC) | 26.3 | 7.8 |
| Crospovidone | 6.7 | 2.0 |
| Sucralose | 4.0 | 1.2 |
| Ascorbic acid | 3.0 | 0.9 |
| Strawberry flavor | 1.2 | 0.4 |
| Colloidal silicon dioxide | 1.6 | 0.5 |
| Sodium stearyl fumarate | 1.7 | 0.5 |
| Red oxide | 0.6 | 0.2 |
| Total | 169 | 50.3 |
| Total Tablet Weight | 336 mg | |

TABLE 11

Exemplary Orally Disintegrating Tablet

| | Formulation 9 | |
|---|---|---|
| Layer and Materials | Mg/tab | Wt %/coating |
| Core | | |
| Seed (Sugar spheres) | 17.7 | 36.8 |
| Omeprazole | 20.0 | 41.5 |
| HPMC | 10.0 | 20.8 |
| Sodium Stearate | 0.45 | 0.9 |
| Total | 48.15 | 100 |
| Subcoating Layer | | |
| HPMC | 15.0 | 55.9 |
| Mannitol | 10.0 | 37.2 |
| Talc | 1.85 | 6.9 |
| Total | 26.85 | 100 |
| Enteric Coating Layer | | |
| HPMC phthalate | 47.0 | 72.3 |
| Cetyl alcohol | 8.5 | 13.1 |
| Triethyl citrate | 4.0 | 6.2 |
| Talc | 4.5 | 6.9 |
| Titanium dioxide | 1.0 | 1.5 |
| Total | 65 | 100 |
| Coating with a Reverse Enteric Polymer | | |
| Amino methacrylate copolymer (a methyl methacrylate-butyl methacrylate-dimethylaminoethyl methacrylate copolymer) | 26.0 | 96.3 |
| Colloidal silicon dioxide | 0.75 | 2.8 |
| Ferric oxide | 0.25 | 0.9 |
| Total | 27 | 100 |
| Additional Tableting Excipients | | |
| | Mg/tab | Wt %/tab |
| Pharmaburst ® | 103.7 | 30.9 |
| Microcrystalline cellulose (MCC) | 26.3 | 7.8 |
| Crospovidone | 26.9 | 8.0 |
| Sucralose | 4.0 | 1.2 |
| Ascorbic acid | 3.0 | 0.9 |
| Strawberry flavor | 1.2 | 0.4 |
| Colloidal silicon dioxide | 1.6 | 0.5 |
| Sodium stearyl fumarate | 1.7 | 0.5 |
| Red oxide | 0.6 | 0.2 |
| Total | 169 | 50.3 |
| Total Tablet Weight | 336 mg | |

TABLE 12

Exemplary Orally Disintegrating Tablet

| | Formulation 10 | |
|---|---|---|
| Layer and Materials | Mg/tab | Wt %/coating |
| Core | | |
| Seed (Sugar spheres) | 17.7 | 36.8 |
| Omeprazole | 20.0 | 41.5 |
| HPMC | 10.0 | 20.8 |

TABLE 12-continued

| | | |
|---|---|---|
| Sodium Stearate | 0.45 | 0.9 |
| Total | 48.15 | 100 |

Subcoating Layer

| | | |
|---|---|---|
| HPMC | 15.0 | 55.9 |
| Mannitol | 10.0 | 37.2 |
| Talc | 1.85 | 6.9 |
| Total | 26.85 | 100 |

Enteric Coating Layer

| | | |
|---|---|---|
| HPMC phthalate | 47.0 | 72.3 |
| Cetyl alcohol | 8.5 | 13.1 |
| Triethyl citrate | 4.0 | 6.2 |
| Talc | 4.5 | 6.9 |
| Titanium dioxide | 1.0 | 1.5 |
| Total | 65 | 100 |

Coating with a Reverse Enteric Polymer

| | | |
|---|---|---|
| Amino methacrylate copolymer (a methyl methacrylate-butyl methacrylate-dimethylaminoethyl methacrylate copolymer) | 26.0 | 96.3 |
| Colloidal silicon dioxide | 0.75 | 2.8 |
| Ferric oxide | 0.25 | 0.9 |
| Total | 27 | 100 |

Additional Tableting Excipients

| | Mg/tab | Wt %/tab |
|---|---|---|
| Pharmaburst ® | 118.9 | 35.4 |
| Microcrystalline cellulose (MCC) | 26.3 | 7.8 |
| Crospovidone | 6.7 | 2.0 |
| Sucralose | 4.0 | 1.2 |
| Ascorbic acid | 3.0 | 0.9 |
| Strawberry flavor | 1.2 | 0.4 |
| Colloidal silicon dioxide | 1.6 | 0.5 |
| Sodium stearyl fumarate | 6.7 | 2.0 |
| Red oxide | 0.6 | 0.2 |
| Total | 169 | 50.3 |
| Total Tablet Weight | | 336 mg |

TABLE 13

Exemplary Orally Disintegrating Tablet

| | Formulation 11 | |
|---|---|---|
| Layer and Materials | Mg/tab | Wt %/coating |

Core

| | | |
|---|---|---|
| Seed (Sugar spheres) | 18.2 | 37.7 |
| Omeprazole | 20.0 | 41.4 |
| HPMC | 10.0 | 20.7 |
| Sodium Stearate | 0.1 | 0.2 |
| Total | 48.3 | 100 |

Subcoating Layer

| | | |
|---|---|---|
| HPMC | 15.1 | 56.6 |
| Mannitol | 10.1 | 37.8 |
| Talc | 1.5 | 5.6 |
| Total | 26.7 | 100 |

Enteric Coating Layer

| | | |
|---|---|---|
| HPMC phthalate | 46.7 | 72.4 |
| Cetyl alcohol | 8.4 | 13.0 |
| Triethyl citrate | 3.8 | 5.9 |
| Talc | 4.6 | 7.1 |
| Titanium dioxide | 1.0 | 1.6 |
| Total | 64.5 | 100 |

Coating with a Reverse Enteric Polymer

| | | |
|---|---|---|
| Amino methacrylate copolymer (a methyl methacrylate-butyl methacrylate-dimethylaminoethyl methacrylate copolymer) | 46.1 | 48.1 |
| Triethyl citrate | 4.7 | 4.9 |
| Talc | 43.9 | 45.8 |
| Colloidal silicon dioxide | 0.9 | 0.9 |
| Sucralose | 0.2 | 0.2 |
| Total | 95.8 | 100 |

Additional Tableting Excipients

| | Mg/tab | Wt %/tab |
|---|---|---|
| Pharmaburst(R) | 136.0 | 32.4 |
| Crospovidone | 25.0 | 6.0 |
| Sucralose | 6.0 | 1.4 |
| Ascorbic acid | 4.1 | 1.0 |
| Mint flavor | 3.1 | 0.7 |
| Colloidal silicon dioxide | 2.1 | 0.5 |
| Sodium stearyl fumarate | 8.4 | 2.0 |
| Total | 184.7 | 44.0 |
| Total Tablet Weight | | 420 mg |

TABLE 14

Results of Exemplary Orally Disintegrating Tablets

| | Tablet Thickness (mm) | Friability (%) | Disintegration (seconds) | Hardness (N) | Compression force (kN) | Ejection force (N) |
|---|---|---|---|---|---|---|
| Formulation 1 | 4.8 | 0.01 | 17 | 41 | 16.1 | 164 |
| Formulation 2 | 4.7 | 0.00 | 18 | 40 | 17.3 | 120 |
| Formulation 3 | 4.6 | 0.00 | 20 | 31 | 22.4 | 118 |
| Formulation 4 | 4.4 | 0.11 | 10 | 31 | 28.6 | 79 |
| Formulation 5 | 4.8 | 0.00 | 13 | 30 | 29.0 | 115 |
| Formulation 6 | 4.4 | 0.06 | 9 | 34 | 24.1 | 78 |
| Formulation 7 | 4.4 | 0.09 | 34 | 40 | 40.4 | 72 |

TABLE 14-continued

Results of Exemplary Orally Disintegrating Tablets

|  | Tablet Thickness (mm) | Friability (%) | Disintegration (seconds) | Hardness (N) | Compression force (kN) | Ejection force (N) |
| --- | --- | --- | --- | --- | --- | --- |
| Formulation 8 | 4.3 | 0.01 | 37 | 44 | 32.7 | 264 |
| Formulation 9 | 4.4 | 0.01 | 14 | 39 | 28.1 | 260 |
| Formulation 10 | 4.4 | 0.01 | 30 | 39 | 37.9 | 77 |
| Formulation 11 | 4.6 | 0.00 | 18 | 34 | 31.0 | 94 |

Example 2

Several comparative batches of orally disintegrating tablet compositions shown in Table 15 were prepared and tested to determine the effect of a reverse enteric polymer coating layer on the friability and/or hardness of an orally disintegrating tablet.

Two separate batches of formulation A (cores containing reverse enteric polymer coating according to the disclosure) were prepared with a compression force of 36 kN and an ejection force of 80 N. A single batch of formulation B (cores containing reverse enteric polymer coating according to the disclosure) was prepared with a compression force of about 40 kN and an ejection force of 72 N. Two separate batches of formulation C (cores devoid of reverse enteric polymer coating) were prepared with a compression force of 36 kN or 44 kN and an ejection force of about 80 N. A single batch of formulation D (cores devoid of reverse enteric polymer coating) was prepared with a compression force of about 52 kN and an ejection force of about 80 N. Each batch of prepared compressed tablets was assayed for weight, disintegration time, thickness, hardness, and friability.

Each batch of the prepared orally disintegrating tablets corresponding to Formulations A, B, C, and D demonstrated rapid disintegration. However, formulations A and B, which also contain a coating having a reverse enteric polymer over the enteric coating of the cores, unexpectedly demonstrated increased tablet hardness and reduced friability as shown in Table 16. This reverse enteric polymer coating surprisingly functioned to increase the compressibility of the tablets.

Thus, formulations having no reverse enteric polymer over-coating did not show acceptable friability and most of the tablets did not withstand the friability measurement and were broken. One batch of formulation C did not break during friability testing and showed friability of 0.97%, but had lower tablet hardness than formulation A or B. The lower hardness was observed even though the tablets were generated with a higher compression force (i.e., 44 kN vs. 36 or 40 kN). In contrast, tablets with enteric coated cores having a reverse enteric polymer over-coating showed low friability levels. This finding was particularly evident when the same compression force of 36 kN was applied to the tablets (Table 16). These results indicate that a reverse enteric polymer coating unexpectedly and advantageously increased the compressibility of the formulation and hence its stability.

TABLE 15

Exemplary Comparative Orally Disintegrating Tablet Compositions

| | Formulation A | | Formulation B | | Formulation C | | Formulation D | |
| --- | --- | --- | --- | --- | --- | --- | --- | --- |
| Layer and Materials | Mg/ tab | Wt %/ coating | Mg/ tab | Wt %/ coating | Mg/ tab | Wt %/ coating | Mg/ tab | Wt %/ coating |
| Core | | | | | | | | |
| Seed (Sugar spheres) | 17.7 | 36.8 | 17.7 | 36.8 | 17.7 | 36.8 | 17.7 | 36.8 |
| Omeprazole | 20.0 | 41.5 | 20.0 | 41.5 | 20.0 | 41.5 | 20.0 | 41.5 |
| HPMC | 10.0 | 20.8 | 10.0 | 20.8 | 10.0 | 20.8 | 10.0 | 20.8 |
| Sodium Stearate | 0.45 | 0.9 | 0.45 | 0.9 | 0.45 | 0.9 | 0.45 | 0.9 |
| Total | 48.2 | 100 | 48.2 | 100 | 48.2 | 100 | 48.2 | 100 |
| Subcoating Layer | | | | | | | | |
| HPMC | 15.0 | 55.9 | 15.0 | 55.9 | 15.0 | 55.9 | 15.0 | 55.9 |
| Mannitol | 10.0 | 37.2 | 10.0 | 37.2 | 10.0 | 37.2 | 10.0 | 37.2 |
| Talc | 1.85 | 6.9 | 1.85 | 6.9 | 1.85 | 6.9 | 1.85 | 6.9 |
| Total | 26.9 | 100 | 26.9 | 100 | 26.9 | 100 | 26.9 | 100 |
| Enteric Coating Layer | | | | | | | | |
| HPMC phthalate | 47.0 | 72.3 | 47.0 | 72.3 | 47.0 | 72.3 | 47.0 | 72.3 |
| Cetyl alcohol | 8.5 | 13.1 | 8.5 | 13.1 | 8.5 | 13.1 | 8.5 | 13.1 |
| Triethyl citrate | 4.0 | 6.2 | 4.0 | 6.2 | 4.0 | 6.2 | 4.0 | 6.2 |

TABLE 15-continued

| | | | | | | | | |
|---|---|---|---|---|---|---|---|---|
| Talc | 4.5 | 6.9 | 4.5 | 6.9 | 4.5 | 6.9 | 4.5 | 6.9 |
| Titanium dioxide | 1.0 | 1.5 | 1.0 | 1.5 | 1.0 | 1.5 | 1.0 | 1.5 |
| Total | 65 | 100 | 65 | 100 | 65 | 100 | 65 | 100 |
| Coating with a Reverse Enteric Polymer | | | | | | | | |
| Amino methacrylate copolymer (a methyl methacrylate-butyl methacrylate-dimethylaminoethyl methacrylate copolymer) | 26.0 | 96.3 | 26.0 | 96.3 | 0 | 0 | 0 | 0 |
| Colloidal silicon dioxide | 0.75 | 2.8 | 0.75 | 2.8 | 0 | 0 | 0 | 0 |
| Ferric oxide | 0.25 | 0.9 | 0.25 | 0.9 | 0 | 0 | 0 | 0 |
| Total | 27 | 100 | 27 | 100 | 0 | 0 | 0 | 0 |

Additional Tableting Excipients

| | Formulation A | | Formulation B | | Formulation C | | Formulation D | |
|---|---|---|---|---|---|---|---|---|
| Matrix Excipients | Mg/tab | Wt %/tab | Mg/tab | Wt %/tab | Mg/tab | Wt %/tab | Mg/tab | Wt %/tab |
| Microcrystalline cellulose | 26.3 | 7.8 | 26.3 | 7.8 | 26.3 | 8.5 | 22.0 | 7.8 |
| Pharmaburst ® | 106.4 | 31.7 | 98.7 | 29.4 | 106.4 | 34.4 | 89.2 | 31.7 |
| Crospovidone | 19.2 | 5.7 | 26.9 | 8.0 | 19.2 | 6.2 | 16.1 | 5.7 |
| Sucralose | 4.0 | 1.2 | 4.0 | 1.2 | 4.0 | 1.3 | 3.4 | 1.2 |
| Ascorbic acid | 3.0 | 0.9 | 3.0 | 0.9 | 3.0 | 1.0 | 2.5 | 0.9 |
| Strawberry flavor | 1.2 | 0.4 | 1.2 | 0.4 | 1.2 | 0.4 | 1.0 | 0.4 |
| Colloidal silicon dioxide | 1.6 | 0.5 | 1.6 | 0.5 | 1.6 | 0.5 | 1.3 | 0.5 |
| Sodium stearyl fumarate | 6.7 | 2.0 | 6.7 | 2.0 | 6.7 | 2.2 | 5.6 | 2.0 |
| Ferric oxide | 0.6 | 0.2 | 0.6 | 0.2 | 0.6 | 0.2 | 0.5 | 0.2 |
| Total | 169 | 50.2 | 169 | 50.3 | 169 | 54.6 | 141.6 | 50.2 |
| Total Tablet Weight | 336 mg | | 336 mg | | 309 mg | | 281.6 mg | |

TABLE 16

Results of Exemplary Comparative Orally Disintegrating Tablet Compositions

| | Tablet Thickness (mm) | Friability (%) | Disintegration (seconds) | Hardness (N) | Compression force (kN) | Ejection force (N) |
|---|---|---|---|---|---|---|
| Formulation A | 4.4 | 0.00 | 23 | 39 | 36 | 80 |
| Formulation A | 4.4 | 0.04 | 29 | 42 | 36 | 73 |
| Formulation B | 4.4 | 0.09 | 34 | 40 | 40 | 72 |
| Formulation C | 3.90 | broken | 5 | 19 | 36 | 82 |
| Formulation C | 3.95 | 0.97 | 7 | 22 | 44 | 78 |
| Formulation D | 3.70 | broken | 5 | 16 | 52 | 80 |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A compressed orally disintegrating tablet comprising a disintegrant and a plurality of units comprising:

i) a plurality of cores comprising a therapeutically effective amount of a proton pump inhibitor;
  ii) an enteric coating over the cores; and
  iii) a coating comprising a reverse enteric polymer in an amount of 5% to 15% by weight of a total tablet weight over the enteric coating;

wherein the disintegrant and the plurality of units are compressed to an orally disintegrating tablet having a friability of 0.75% or less when 10 kN to 50 kN of a compression force is applied during manufacturing of the tablet.

2. The tablet of claim 1, wherein each core comprises an inert seed coated with an active ingredient coating comprising a proton pump inhibitor.

3. The tablet of claim 2, wherein the inert seed comprises a granule, a pellet, a bead, or a powder.

4. The tablet of claim 1, wherein each unit further comprises a subcoating between the plurality of cores and the enteric coating.

5. The tablet of claim 4, wherein the subcoating comprises one or more of hydroxypropyl methylcellulose, hydroxypropyl cellulose, polyvinylpyrrolidone, polyethylene glycol, polyvinyl alcohol or a mixture or combination thereof.

6. The tablet of claim 1, wherein the enteric coating comprises one or more of cellulose acetate phthalate (CAP), hydroxypropyl methylcellulose phthalate (HPMCP), hydroxypropyl methylcellulose acetate succinate (HPMCAS), polyvinyl acetate phthalate, cellulose acetate trimellitate, shellac, polymethacrylic acid, polymethyl methacrylate, polyethyl methacrylate, polyethyl acrylate or a mixture or combination thereof.

7. The tablet of claim 1, wherein the coating comprising a reverse enteric polymer comprises a (meth)acrylate polymer or copolymer.

8. The tablet of claim 1, wherein the reverse enteric polymer comprises a methyl methacrylate-butyl methacrylate-dimethylaminoethyl methacrylate copolymer.

9. The tablet of claim 1, wherein the reverse enteric polymer is in an amount of 70% to 100% of the total reverse enteric coating mass.

10. The tablet of claim 1, wherein the weight percentage ratio of the coating comprising a reverse enteric polymer to the enteric coating is 0.4:1.

11. The tablet of claim 1, wherein the disintegrant comprises one or more of crospovidone, croscarmellose sodium, a cellulose derivative, cross-linked derivatives of starch, pregelatinized starch, crosslinked sodium carboxymethyl cellulose, low substituted hydroxypropylcellulose or a mixture or combination thereof.

12. The tablet of claim 1, further comprising one or more pharmaceutically acceptable excipients selected from a binder, a filler, a diluent, a surfactant, a glidant, a lubricant, a plasticizer, an anti-tacking agent, an alkaline substance, a tonicity enhancing agent, a wetting agent, a buffering substance, a preservative, a sweetener, an opacifier, a colorant, and a mixture or combination thereof.

13. The tablet of claim 1 having a hardness of 20 N to 100 N.

14. The tablet of claim 1, which substantially disintegrates in an oral cavity of a subject within less than 60 seconds after administration.

15. The tablet of claim 1, wherein the disintegrant is in an amount of 2% to 25% by weight of a total tablet weight; or wherein the plurality of cores is in an amount of 5% to 25% by weight of a total tablet weight; or wherein the enteric coating is in an amount of 10% to 30% by weight of a total tablet weight.

16. The tablet of claim 4, wherein the subcoating is in an amount of 2% to 15% by weight of the total tablet weight.

17. A process of manufacturing the tablet of claim 1 comprising:
a) generating a plurality of cores comprising a therapeutically effective amount of a proton pump inhibitor;
b) applying a solution or dispersion comprising an enteric polymer to the plurality of cores of step (a) thereby obtaining a plurality of enteric coated cores;
c) applying a solution or dispersion comprising a reverse enteric polymer to the enteric coated cores of step (b) thereby obtaining a plurality of units;
d) mixing the plurality of units of step (c) with at least one tablet excipient comprising a disintegrant thereby obtaining a blend; and
e) compressing the blend of step (d) thereby obtaining the compressed orally disintegrating tablet.

18. The process of claim 17, wherein step (a) comprises applying a solution or dispersion comprising a therapeutically effective amount of a proton pump inhibitor to a plurality of inert seeds.

19. The process of claim 17, further comprising an additional step prior to the step (b) comprising:
a1) applying a solution or dispersion comprising one or more of hydroxypropyl methylcellulose, hydroxypropyl cellulose, polyvinylpyrrolidone, polyethylene glycol, polyvinyl alcohol or a mixture or combination thereof to the plurality of cores of step (a) thereby obtaining a subcoating between the cores and the enteric coating.

20. A compressed orally disintegrating tablet prepared by a process comprising the following steps:
a) generating a plurality of cores comprising a therapeutically effective amount of a proton pump inhibitor;
b) applying a solution or dispersion comprising an enteric polymer to the plurality of cores of step (a) thereby obtaining a plurality of enteric coated cores;
c) applying a solution or dispersion comprising a reverse enteric polymer to the enteric coated cores of step (b) thereby obtaining a plurality of units;
d) mixing the plurality of units of step (c) with at least one tablet excipient comprising a disintegrant thereby obtaining a blend; and
e) compressing the blend of step (d) thereby obtaining the compressed orally disintegrating tablet,
wherein the coating comprising a reverse enteric polymer is in an amount of 5% to 15% by weight of a total tablet weight; and
wherein a friability of the compressed tablet is 0.75% or less when 10 kN to 50 kN of a compression force is applied during manufacturing of the tablet.

21. A method of treating a subject having a gastric disorder comprising gastric reflux, gastroesophageal reflux disease, laryngopharyngeal reflux, laryngitis, dyspepsia, Barrett's esophagus, eosinophilic esophagitis, gastritis, gastrinomas, Zollinger-Ellison syndrome, peptic ulcers, or excessive *Helicobacter pylori* or combinations thereof, the method comprising administering the tablet of claim 1 to the subject.

22. A method for increasing a compressibility of a compressed orally disintegrating tablet comprising a disintegrant and a plurality of units comprising:
i) a plurality of cores comprising a therapeutically effective amount of a proton pump inhibitor; and
ii) an enteric coating over the cores;
the method comprising the step of applying a coating comprising a reverse enteric polymer in an amount of 5% to 15% by weight of a total tablet weight to the enteric coated cores, wherein the increased compressibility comprises one or more of a decreased friability or an increased hardness compared to a compressed orally disintegrating tablet not comprising a coating comprising a reverse enteric polymer when a substantially identical compression force is applied during manufacturing of the tablet.

23. The method of claim 22, wherein the decreased friability is 0.75% or less, or wherein the increased hardness is 20 N to 100 N when 10 kN to 50 kN of compression force is applied during manufacturing of the tablet.

24. A compressed orally disintegrating tablet comprising a disintegrant in an amount of 2% to 25% by weight of a total tablet weight, and a plurality of units comprising:
   i) a plurality of cores comprising a therapeutically effective amount of a proton pump inhibitor, the plurality of cores in an amount of 5% to 25% by weight of a total tablet weight;
   ii) a subcoating over the cores, the subcoating in an amount of 2% to 15% by weight of a total tablet weight;
   iii) an enteric coating over the subcoating, the enteric coating in an amount of 10% to 30% by weight of a total tablet weight; and
   iv) a coating comprising a reverse enteric polymer over the enteric coating, the reverse enteric coating in an amount of 5% to 15% by weight of a total tablet weight;
wherein the orally disintegrating tablet optionally comprises one or more additional excipients selected from the group consisting of a binder, a filler, a diluent, a surfactant, a glidant, a lubricant, a plasticizer, an anti-tacking agent, an alkaline substance, a tonicity enhancing agent, a wetting agent, a buffering substance, a preservative, a flavoring agent, an opacifier, a colorant, an anti-oxidant or a mixture or combination thereof in an amount of not more than 50% by weight of a total tablet weight, wherein the weight of all components add to 100% (w/w), and
wherein a friability of the compressed tablet is 0.75% or less when 10 kN to 50 kN of a compression force is applied during manufacturing of the tablet.

25. The tablet of claim 24, wherein the disintegrate comprises crospovidone; the plurality of cores comprises an inert seed coated with a drug layer comprising omeprazole or a pharmaceutically acceptable salt thereof, hydroxypropylmethyl cellulose, and sodium stearate; the subcoating comprises hydroxypropylmethyl cellulose, and mannitol; the enteric coating comprises hydroxypropylmethyl cellulose phthalate, cetyl alcohol, and triethyl citrate; and the reverse enteric coating comprises an amino methacrylate copolymer.

26. The tablet of claim 1 providing a delayed release profile of the proton pump inhibitor.

* * * * *